United States Patent
Yanagi et al.

[11] Patent Number: 5,935,907
[45] Date of Patent: Aug. 10, 1999

[54] PHENYLACETYLENE DERIVATIVES

[75] Inventors: Akihiko Yanagi, Tochigi; Shin-ichi Narabu, Ibaraki; Toshio Goto, Tochigi; Seishi Ito, Tochigi; Natsuko Minegishi, Tochigi; Tatsuya Yamaoka, Tochigi; Chieko Ueno, Tochigi, all of Japan

[73] Assignee: Nihon Bayer Agrochem K.K., Tokyo, Japan

[21] Appl. No.: 09/047,260

[22] Filed: Mar. 24, 1998

[30] Foreign Application Priority Data

Mar. 31, 1997 [JP] Japan .................................. 9-094386
Aug. 8, 1997 [JP] Japan .................................. 9-225625

[51] Int. Cl.⁶ ...................... C07D 413/04; C07D 417/04; A01N 43/80
[52] U.S. Cl. .................. 504/242; 504/243; 504/239; 544/298; 544/309; 544/311; 544/313; 544/314
[58] Field of Search ...................... 544/298, 309, 544/311, 313, 314; 504/242, 243

[56] References Cited

U.S. PATENT DOCUMENTS

| | | | |
|---|---|---|---|
| 3,644,355 | 2/1972 | Ebner et al. | 260/250 |
| 4,069,038 | 1/1978 | Teach | 71/95 |
| 4,620,865 | 11/1986 | Beck et al. | 71/67 |
| 4,640,707 | 2/1987 | Nagano et al. | 71/96 |
| 4,820,334 | 4/1989 | Shida et al. | 71/92 |
| 4,828,604 | 5/1989 | Kume et al. | 71/90 |
| 4,919,707 | 4/1990 | Shida et al. | 71/92 |
| 4,941,909 | 7/1990 | Wenger et al. | 71/92 |
| 4,964,905 | 10/1990 | Kouji et al. | 71/95 |
| 4,973,353 | 11/1990 | Shida et al. | 71/92 |
| 5,032,165 | 7/1991 | Miura et al. | 71/92 |
| 5,244,863 | 9/1993 | Kawamura et al. | 504/216 |
| 5,298,502 | 3/1994 | Halling et al. | 514/185 |
| 5,312,798 | 5/1994 | Kawamura et al. | 504/134 |
| 5,407,808 | 4/1995 | Halling et al. | 435/34 |
| 5,411,935 | 5/1995 | Takemura et al. | 504/243 |
| 5,484,763 | 1/1996 | Wepplo | 504/269 |
| 5,523,278 | 6/1996 | Wepplo | 504/271 |

FOREIGN PATENT DOCUMENTS

| | | | |
|---|---|---|---|
| WO 94/13652 | 6/1994 | WIPO | C07D 272/14 |
| WO 95/33718 | 12/1995 | WIPO | C07D 207/24 |
| WO 95/33719 | 12/1995 | WIPO | C07D 207/26 |

OTHER PUBLICATIONS

Stolle et al., (CA 113:23826, abstract of Tetrahederon (1989), 45 (20), 6511–18.
Forbes et al., (CA 119:49269, abstract of Synth. Commun. (1993), 23 (6), 715–23.
Klinzt et al., (CA 124:261065, abstract of DE 4,424,791), 1996.
Stolle et al., (CA 114:246542, abstract of Tetrahederon (1991), 47 (9), 1753–64).
Derwent Abstract 87–260938: English Abstract of JP Sho. 62–181283–A (1986).
Derwent Abstract 89–274534: English Abstract of JP Hei. 1–199978–A (1988).
Derwent Abstract 91–249443: English Abstract of JP Hei. 3–163063–A (1988).
Derwent Abstract 93–363700: English Abstract of FR 2660308 (1990).
Derwent Abstract 92–187701: English Abstrct of JP Hei. 4–117355–A (1990).
Derwent Abstract 94–083067: English Abstract of WO 94/04511 (1992).
Derwent Abstract 95–167233: English Abstract of JP Hei. 7–89941–A (1993).
Derwent Abstract 95–290225: English Abstract of JP Hei. 7–187919–A (1993).
Derwent Abstract 95–295088: English Abstract of JP Hei. 7–188220–A (1993).
Derwent Abstract 95–295089: English Abstract of JP Hei. 7–188221–A (1993).
Derwent Abstract 96–354458: English Abstract of JP Hei. 8–259564–A (1993).

*Primary Examiner*—Jose' G. Dees
*Assistant Examiner*—Sabiha N. Qazi
*Attorney, Agent, or Firm*—Sprung Kramer Schaefer & Briscoe

[57] ABSTRACT

The invention is related to a novel phenylacetylene derivates of formula:

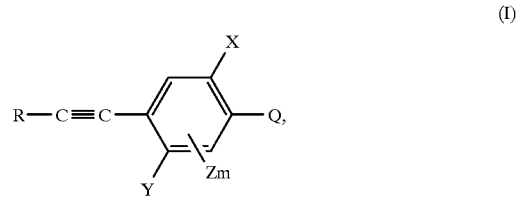

(I)

wherein X represents hydrogen, halogen, optionally substituted $C_{1-6}$ alkyl; Y represents hydrogen, halogen, cyano, nitro, optionally substituted $C_{1-6}$ alkyl, $C_{1-6}$ alkoxy, $C_{3-8}$ cycloalkoxy, optionally substituted $C_{1-6}$ alkylthio, $C_{3-8}$ cycloalkylthio, $C_{1-6}$ alkylsulfinyl, optionally substituted $C_{1-6}$ alkylsulfonyl, $C_{3-8}$ cycloalkylsulfonyl, $C_{1-6}$ alkylsulfonyloxy, optionally substituted sulfonamide, optionally substituted carboxamide, etc., or Y may form together with Z which is bonded to the vicinal carbon atom a 5- or 6-membered ring; n is 0 or 1; Z represents hydrogen or halogen; m is 1 or 2; R represents hydrogen, halogen, $C_{1-6}$ alkyl, tri($C_{1-6}$ alkyl)silyl, $COOR^c$ or $CONR^dR^e$; Q represents a heterocyclic group, and their use as herbicid.

5 Claims, No Drawings

PHENYLACETYLENE DERIVATIVES

The present invention relates to novel phenylacetylene derivatives, to processes for their preparation and to their use as herbicides.

It has already been known that certain heterocyclic compounds comprising a substituted phenyl moiety have herbicidal activity (see e.g. Japanese Patent Official Announcement (kohyo) Hei 2-501309; Japanese Patent Kokai Publications Sho 60-172967, Sho 61-2659, Sho 61-43188, Sho 61-212558, Sho 62-181283, Sho 63-152366, Sho 63-230678, Sho 63-313779, Hei 1-56674, Hei 1-199978, Hei 4-117355, Hei 4-217968, Hei 6-321941, Hei 7-89313, Hei 7-89941, Hei i-187919, Hei 7-188220, Hei 7-188221, Hei 8-253476, Hei 8-259546; EP-A 361114; DE-A 1695840, DE-A 2612731; FR-A 2660308, U.S. Pat. No. 5,136,868, U.S. Pat. No. 5,310,723, WO90/06748, WO94/0451 1, WO94/13652, WO95/33718, WO95/33719).

There have now been found novel phenylacetylene derivatives of formula (I).

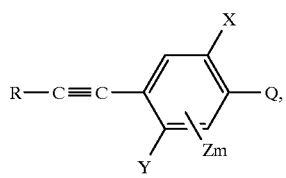

(I)

wherein

X represents hydrogen, halogen, $C_{1-6}$ alkyl or $C_{1-6}$ haloalkyl,

Y represents hydrogen, hydroxy, halogen, cyano, nitro, $C_{1-6}$ alkyl $C_{1-6}$ haloalkyl, $C_{1-6}$ alkoxy, $C_{3-8}$ cycloalkoxy, $C_{1-6}$ haloalkoxy, $C_{1-3}$ alkoxy-$C_{1-3}$ alkoxy, $C_{1-6}$ alkylthio, $C_{3-8}$ cycloalkylthio, $C_{1-6}$ haloalkylthio, $C_{1-6}$ alkylsulfinyl, $C_{1-6}$ alkylsulfonyl, $C_{3-8}$ cycloalkylsulfonyl, $C_{1-6}$ haloalkylsulfonyl, $C_{1-6}$ alkylsulfonyloxy, $C_{3-6}$ alkenyloxy, $C_{3-6}$ alkynyloxy, a group $SO_2NR^aR^b$, a group $COOR^c$, a group $CONR^dR^e$, optionally substituted amino, a group $A^1$—$(CH_2)n$—$CHR^f$—$COOR^g$, $C_{1-3}$ alkoxycarbonyl-$C_{1-3}$ alkyl or $C_{1-3}$ alkoxycarbonyl-$C_{1-3}$ haloalkyl, or Y may form a 5- or 6-membered ring together with Z which is vicinal to the carbon atom of Y, $R^a$ and $R^b$ each represent independently hydrogen or $C_{1-6}$ alkyl, or $R^a$ and $R^b$ may form together with the N atom to which they are bonded a 5- or 6-membered heterocyclic group, $R^c$ represents hydrogen, an alkali metal, an alkaline earth metal, $C_{1-6}$ alkyl or $C_{1-4}$ alkoxy-carbonyl-$C_{1-4}$ alkyl, $R^d$ represents hydrogen or $C_{1-6}$ alkyl, $R^e$ represents hydrogen or $C_{1-6}$ alkyl, $R^f$ represents hydrogen, halogen or $C_{1-6}$ alkyl, $R^g$ represents hydrogen, an alkali metal, an alkaline earth metal or $C_{1-6}$ alkyl $A^1$ represents oxygen or sulfur, n is 0 or 1, Z represents hydrogen or halogen, m is 1 or 2, R represents hydrogen, halogen, $C_{1-6}$ alkyl, hydroxy-$C_{1-6}$ alkyl, tri($C_{1-6}$ alkyl)silyl, a group $COOR^c$ or a group $CONR^dR^e$, Q represents a heterocyclic group selected from

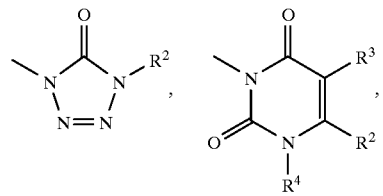

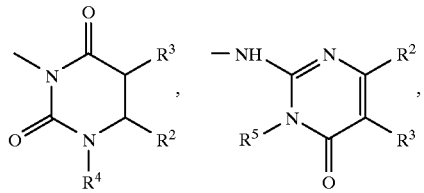

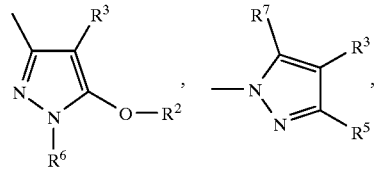

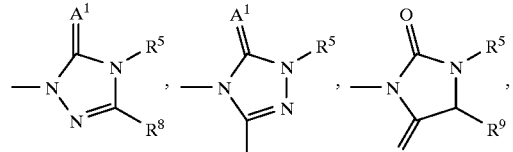

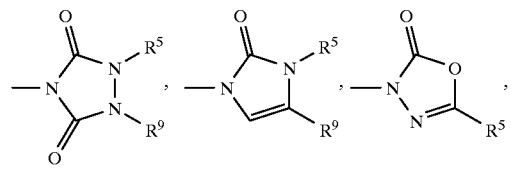

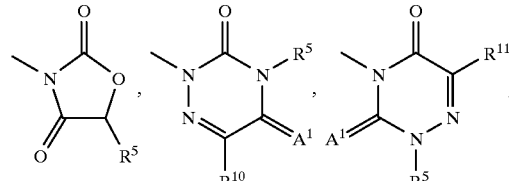

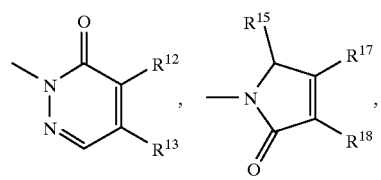

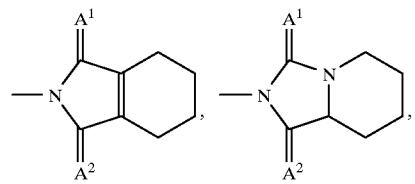

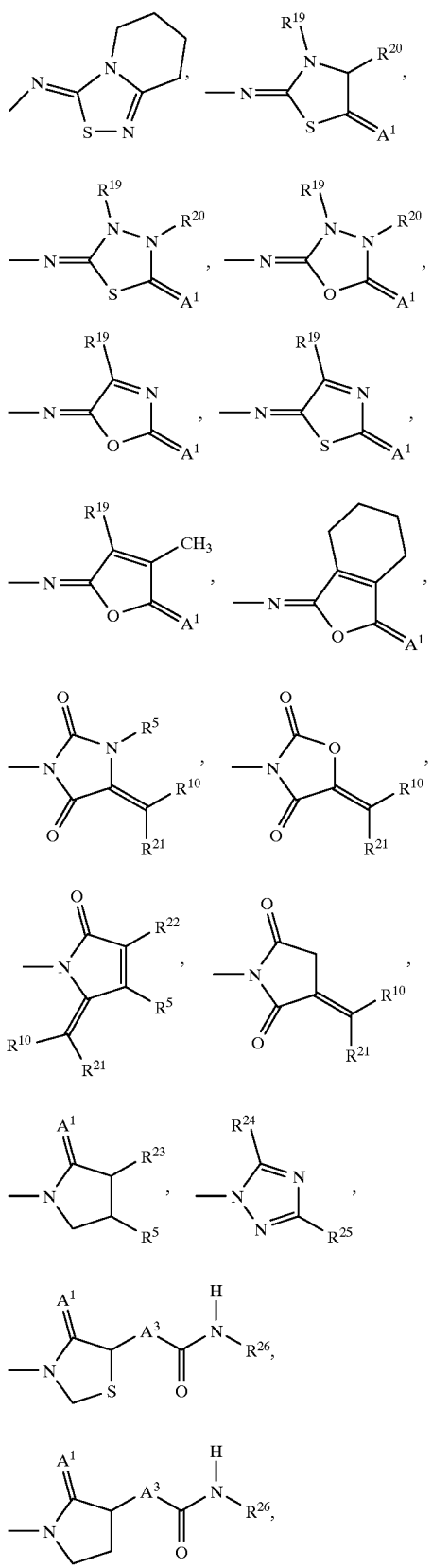
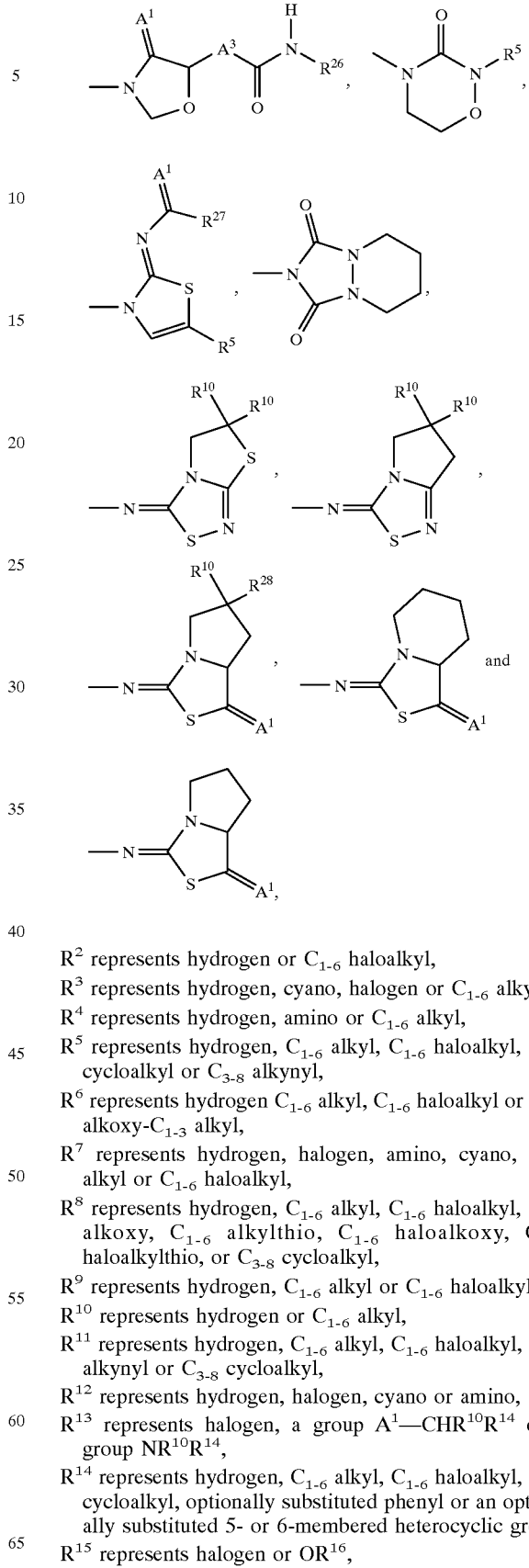

R² represents hydrogen or C₁₋₆ haloalkyl,

R³ represents hydrogen, cyano, halogen or C₁₋₆ alkyl,

R⁴ represents hydrogen, amino or C₁₋₆ alkyl,

R⁵ represents hydrogen, C₁₋₆ alkyl, C₁₋₆ haloalkyl, C₃₋₈ cycloalkyl or C₃₋₈ alkynyl, R⁶ represents hydrogen C₁₋₆ alkyl, C₁₋₆ haloalkyl or C₁₋₃ alkoxy-C₁₋₃ alkyl, R⁷ represents hydrogen, halogen, amino, cyano, C₁₋₆ alkyl or C₁₋₆ haloalkyl, R⁸ represents hydrogen, C₁₋₆ alkyl, C₁₋₆ haloalkyl, C₁₋₆ alkoxy, C₁₋₆ alkylthio, C₁₋₆ haloalkoxy, C₁₋₆ haloalkylthio, or C₃₋₈ cycloalkyl, R⁹ represents hydrogen, C₁₋₆ alkyl or C₁₋₆ haloalkyl, R¹⁰ represents hydrogen or C₁₋₆ alkyl, R¹¹ represents hydrogen, C₁₋₆ alkyl, C₁₋₆ haloalkyl, C₃₋₈ alkynyl or C₃₋₈ cycloalkyl, R¹² represents hydrogen, halogen, cyano or amino, R¹³ represents halogen, a group A¹—CHR¹⁰R¹⁴ or a group NR¹⁰R¹⁴, R¹⁴ represents hydrogen, C₁₋₆ alkyl, C₁₋₆ haloalkyl, C₃₋₈ cycloalkyl, optionally substituted phenyl or an optionally substituted 5- or 6-membered heterocyclic group, R¹⁵ represents halogen or OR¹⁶, $R^{16}$ represents hydrogen or acyl, $R^{17}$ and $R^{18}$ each represent independently hydrogen or $C_{1-6}$ alkyl, $R^{19}$ and $R^{20}$ each represent independently represent hydrogen, $C_{1-6}$ alkyl, $C_{1-6}$ haloalkyl or $C_{3-8}$ cycloalkyl, $R^{21}$ represents hydrogen or $C_{1-6}$ alkyl, $R^{22}$ represents hydrogen, $C_{1-6}$ alkyl or $C_{1-6}$ haloalkyl, $R^{23}$ hydrogen, halogen, cyano, optionally substituted phenyl or a radical $CONR^d R^e$, $R^{24}$ represents $C_{1-6}$ alkyl, $C_{1-6}$ haloalkyl, optionally substituted phenyl or $C_{3-8}$ cycloalkyl, $R^{25}$ represents cyano or a radical $CONR^d R^e$, $R^{26}$ represents $C_{1-6}$ allyl, $C_{1-6}$ haloalkyl, $C_{3-6}$ cycloalkyl, $C_{1-3}$ alkyl-$C_{3-6}$ cycloalkyl, 1-cyano-$C_{3-6}$ cycloalkyl, 1-amino-$C_{3-6}$ cycloalkyl, 1-ethynyl-$C_{3-6}$ cycloalkyl, 1-cyano-$C_{3-5}$ alkyl or 1-ethynyl-$C_{3-5}$ alkyl, $R^{27}$ represents hydrogen, $C_{1-6}$ alkyl, $C_{1-6}$ haloalkyl, $C_{3-6}$ cycloalkyl, $C_{1-6}$ alkoxy, $C_{1-6}$ haloalkoxy or $C_{3-6}$ cycloalkyl-$C_{1-4}$ alkoxy, $R^{28}$ represents hydrogen or halogen, $A^2$ represents oxygen or sulfur, and $A^3$ represents oxygen, sulfur or $CH_2$.

The phenylacetylene derivatives of formula (I) according to the invention can be obtained by the following processes:

(a) In the case where R is a group other than hydrogen: compounds of formula (II)

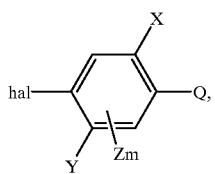

(II)

wherein X, Y, Z, m and Q are defined as above, and hal is bromine or iodine, are reacted with compounds of formula (III)

R'—C≡CH    (III)

wherein R' represents a group as defined for the above R with the exception of hydrogen, if appropriate, in the presence of inert solvents, a catalyst, a promoter and an acid binder, or (b) in the case where R is hydrogen: compounds of formula (Ia)

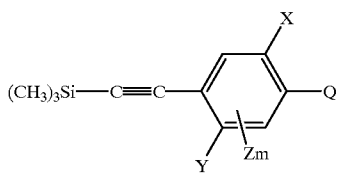

(Ia)

wherein X, Y, Z, m and Q are defined as above are reacted with a desilylating agent in the presence of appropriate diluents.

The phenylacetylene derivatives of formula (I) according to the invention, exhibit powerful herbicidal effects.

Surprisingly, the phenylacetylene derivatives of formula (I) provided by the invention exhibit substantially superior herbicidal effects in comparison with the previously known compounds described in the above prior art literature.

In this specification, the "halogen" and the halogen atoms in the "haloalkyl", "haloalkoxy", "haloalkylthio" and "haloalkylsulfonyl" radicals represent fluorine, chlorine, bromine or iodine, preferably being fluorine, chlorine or bromine.

When these "haloalkyl", "haloalkoxy", "haloalkylthio" and "haloalkylsulfonyl" radicals contain two or more halogen atoms, these halogen atoms may be same or different.

The "alkyl" may be straight-chain or branched and includes, for example, methyl, ethyl, propyl, isopropyl, butyl, isobutyl, sec-butyl, tert-butyl, pentyl, neopentyl, hexyl, 2-ethylhexyl, and the like.

The "haloalkyl" may be straight-chain or branched and includes, for example, chloromethyl, trichloro-methyl, difluoromethyl, trifluoromethyl, chlorodifluoromethyl, 2,2,2-trifluoroethyl, 3-fluoropropyl, 3,3,3-trifluoropropyl, 2,2,3,3-tetrafluoropropyl, 1,1,2,3,3,3-hexafluoropropyl, 2-chloro-1,1-dimethylethyl, 2-fluoro-1,1-dimethylethyl, and the like.

The "alkoxy" may be straight-chain or branched and includes, for example, methoxy, ethoxy, isopropoxy, propoxy, butoxy, isobutoxy, tert-butoxy; pentoxy, and the like.

The "cycloalkyl" includes, for example, cyclopropyl, 1-methylcyclopropyl, 2-methylcyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, cycloheptyl, cyclooctyl, and the like.

The "cycloalkoxy" includes, for example, cyclopropyloxy, 1-methylcyclopropyloxy, 2-methylcyclopropyloxy, cyclobutyloxy, cyclopentyloxy, 2-methylcyclopentyloxy, 3-methylcyclopentyloxy, cyclohexyloxy, 2-methylcyclohexyloxy, 3-methylcyclohexyloxy, 4-methylcyclohexyloxy, cycloheptyloxy, cyclooctyloxy, and the like.

The "haloalkoxy" may be straight-chain or branched and includes, for example, difluoromethoxy, trifluoromethoxy, 2-chloro-1,1,2-trifluoroethoxy, 2,2,2-trifluoroethoxy, and the like.

The "alkylthio" may be straight-chain or branched and includes, for example, methylthio, ethylthio, propylthio, isopropylthio, butylthio, isobutylthio, sec-butylthio, tert-butylthio, pentylthio, neopentylthio, hexylthio, 2-ethylhexylthio, and the like.

The "cycloalkythio" includes, for example, cyclopropylthio, 1-methylcyclopropylthio, cyclopentylthio, 1-methylcyclopentylthio, cyclohexylthio, 1-methylcyclohexylthio, 2-methylcyclohexylthio, 3-methylcyclohexylthio, cycloheptylthio, cyclooctylthio, and 5 the like.

The "haloalkylthio" may be straight-chain or branched and includes, for example, difluoromethylthio, chlorodifluoromethylthio, trifluoromethylthio, 2,2,2-trifluoroethylthio, 3-fluoropropylthio, 3,3,3-trifluoropropylthio, 2,2,3,3-tetrafluoropropylthio, 1,1,2,3,3,3-hexafluoropropylthio, 2-chloro-1,1-dimethylethylthio, 2-fluoro-1,1-dimethylethylthio, and the like.

The "alkylsulfinyl" may be straight-chain or branched and includes, for example, methylsulfinyl, ethylsulfinyl, propylsulfinyl isopropylsulfinyl, butylsulfinyl, isobutylsulfinyl, sec-butylsulfinyl, tert-butylsulfinyl, pentylsulfinyl, neopentylsulfinyl, hexylsulfinyl, 2-ethylhexylsulfinyl, and the like.

The "alkylsulfonyl" may be straight-chain or branched and includes, for example, methylsulfonyl, ethylsulfonyl, propylsulfonyl,. isopropylsulfonyl, butylsulfonyl, isobutylsulfonyl, sec-butylsulfonyl, tert-butylsulfonyl, pentylsulfonyl neopentylsulfonyl, hexylsulfonyl, 2-ethylhexylsulfonyl, and the like.

The "cycloalkylsulfonyl" includes, for example, cyclopropylsulfonyl 1-methylcyclopropylsulfonyl, cyclobutylsulfonyl, cyclopentylsulfonyl, cyclohexylsulfonyl, 1-methylcyclohexylsulfonyl, cycloheptylsulfonyl, cyclooctylsulfonyl, and the like.

The "haloalkylsulfonyl" may be straight-chain or branched and includes, for example, difluoromethylsulfonyl, chlorodifluoromethylsulfonyl, trifluoromethylsulfonyl, and the like.

The "alkylsulfonyloxy" may be straight-chain or branched and includes, for example, methylsulfonyl-oxy, ethylsulfonyloxy, propylsulfonyloxy, isopropylsulfonyloxy, butylsulfonyloxy, isobutylsulfonyl-oxy, sec-butylsulfonyloxy, tert-butylsulfonyloxy, pentylsulfonyloxy, neopentylsulfonyloxy, hexyl-sulfonyloxy, and the like.

The "alkenyloxy" may be straight-chain or branched and includes, for example, allyloxy, butenyloxy, 2-methylallyloxy, and the like.

The "alkynyloxy" may be straight-chain or branched and includes, for example, propargyloxy, and the like.

The "amino" may optionally be mono- or di-substituted by substituent(s) such as $C_{1-6}$ alkyl, $C_{1-6}$ haloalkyl, $C_{2-6}$ alkylcarbonyl $C_{1-6}$ alkylsulfonyl, $C_{3-6}$ cycloalkylsulfonyl, $C_{1-6}$ haloalkyl-sulfonyl, $C_{2-6}$ alkenyl and $C_{2-6}$ alkynyl and includes, for example, amino, acetylamino, trifluoromethylsulfonylamino, methylsulfonylamino, ethylsulfonylamino, bis(methylsulfonyl)amino, 2,2,2-trifluoroethyl-sulfonylamino, N-2-propynyl-N-ethylsulfonylamino, N-2-propenyl-N-ethyl-sulfonylamino, N-methyl-N-ethylsulfonylamino, N-acetyl-N-ethylsulfonylamino, and the like.

The "phenyl" may optionally be substituted by one or more of substituent(s) and examples of the substituents include halogen (fluorine, chlorine, bromine, iodine), $C_{1-6}$ alkyl (e.g., methyl, ethyl, propyl, isopropyl, butyl), $C_{1-6}$ haloalkyl (e.g., chloromethyl, trichloromethyl, difluoromethyl, trifluoromethyl, chlorodifluoromethyl, 2,2,2-trifluoroethyl, 3-fluoropropyl, 3,3,3-trifluoropropyl, 2,2,3,3-tetrafluoropropyl, 1,1,2,3,3,3,-hexafluoropropyl, and the like.

The "5- or 6-membered heterocyclic group" may contain one to four heteroatoms selected from N, S and O in the ring and includes, for instance, pyrazolyl, isoxazolyl, thienyl, pyridyl, and the like. These heterocyclic groups may be substituted by one or more substituent(s) and examples of the substituents include halogen (fluorine, chlorine, bromine, iodine), $C_{1-6}$ alkyl (e.g., methyl, ethyl, propyl, isopropyl, butyl), $C_{1-6}$ haloalkyl (e.g., chloromethyl, trichloromethyl, difluoromethyl, trifluoromethyl, chlorodifluoromethyl, 2,2,2-trifluoroethyl, 3-fluoropropyl, 3,3,3-trifluoropropyl, 2,2,3,3-tetrafluoropropyl, 1,1,2,3,3,3,-hexafluoropropyl), and the like.

Among the compounds of formula (I) according to the invention, preferred phenylacetylene derivatives of formula (I) are those wherein X represents hydrogen, fluorine, chlorine, methyl or trifluoromethyl, Y represents hydrogen, hydroxy, fluorine, chlorine, cyano, nitro, methyl, ethyl, propyl, trifluoromethyl, chlorodifluoromethyl, $C_{1-3}$ alkoxy, $C_{3-6}$ cycloalkoxy, $C_{1-3}$ haloalkoxy, $C_{1-3}$ alkoxy-$C_{1-3}$ alkoxy, $C_{1-3}$ alkylthio, $C_{3-6}$ cycloalkylthio, $C_{1-3}$ haloalkyithio, $C_{1-3}$ alkyl-sulfinyl, $C_{1-3}$ alkylsulfonyl, $C_{3-6}$ cycloalkylsulfonyl, $C_{1-3}$ haloalkylsulfonyl, $C_{1-3}$ alkylsulfonyl-oxy, $C_{3-4}$ alkenyloxy, $C_{3-4}$ alkynyloxy, aminosulfonyl, methyl-aminosulfonyl, ethylaminosulfonyl, diethylaminosulfonyl, 1-pyrrolidinylsulfonyl, a group COORC, aminocarbonyl, amino, acetylamino, trifluoromethylsulfonylamino, methylsulfonylamino, ethylsulfonylamino, bis (methylsulfonyl)amino, bis(ethylsulfonyl)amino, ($C_{1-4}$ alkylcarbonyl)($C_{1-4}$ alkyl-sufonyl)amino, $C_{1-3}$ alkoxycarbonyl-$C_{1-3}$ alkylthio, $C_{1-3}$ alkoxy-carbonyl-$C_{1-3}$ haloalkyl-thio, $C_{1-3}$ alkoxycarbonyl-$C_{1-3}$ alkoxy, $C_{1-3}$ alkoxy-carbonyl-$C_{1-3}$ haloalkoxy, $C_{1-3}$ alkoxycarbonyl-$C_{1-3}$ alkyl or $C_{1-3}$ alkoxycarbonyl-$C_{1-3}$ haloalkyl, $R^c$ represents hydrogen, methyl, ethyl, propyl, methoxycarbonylmethyl, ethoxycarbonylmethyl, 1-(methoxycarbonyl)ethyl or 1-(ethoxycarbonyl)ethyl, $A^1$ represents oxygen or sulfur, n is 0 or 1, Z represents hydrogen, fluorine or chlorine, or Y may form a group —OCR$^h$R$^i$—CH$_2$— or a group —OCR$^h$=CH— together with Z which is vicinal to the carbon atom of Y, $R^h$ represents hydrogen, $C_{1-3}$ alkyl, hydroxy-$C_{1-3}$ alkyl, $C_{1-3}$ alkoxy-$C_{1-3}$ alkyl, carboxy or $C_{1-3}$ alkoxycarbonyl, $R^i$ represents hydrogen or $C_{1-3}$ alkyl, m is 1 or 2, R represents hydrogen, fluorine, methyl, hydroxymethyl, trimethylsilyl, methoxycarbonyl, ethoxycarbonyl or aminocarbonyl, Q represents a heterocyclic group selected from

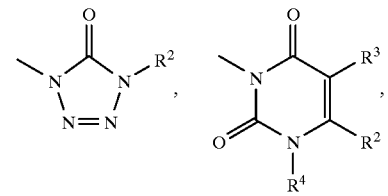

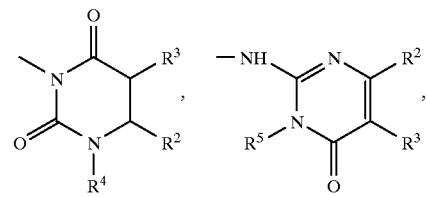

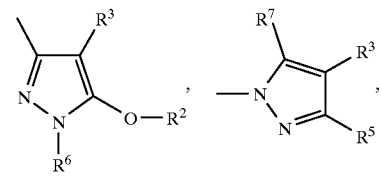

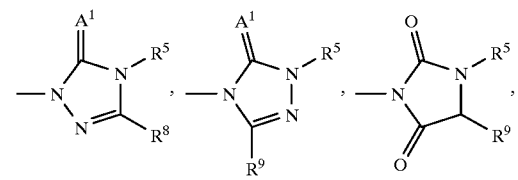

-continued

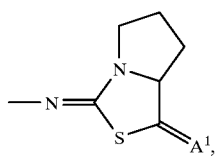, $R^2$ represents hydrogen, trifluoromethyl, difluoromethyl, chlorodifluoromethyl, 2,2,2-trifluoroethyl, 3-fluoropropyl, 3,3,3-trifluoropropyl, 2,2,3,3-tetrafluoropropyl or 1,1,2,3,3,3-hexafluoropropyl, $R^3$ represents hydrogen, cyano, fluorine, chlorine, methyl or ethyl, $R^4$ represents hydrogen, amino, methyl or ethyl, $R^5$ represents hydrogen, methyl, ethyl, isopropyl, tert-butyl, 1-ethyl-1-methylpropyl, 1,1-dimethylpropyl, chloromethyl, difluoromethyl, dichlorofluoromethyl, trifluoromethyl, 3-fluoropropyl, 1,1-dimethyl-2-chloroethyl, 1,1-dimethyl-2-fluoroethyl, cyclopropyl or 1,1-dimethylpropargyl, $R^6$ represents hydrogen, methyl, ethyl, propyl, isopropyl, tert-butyl, 2,2,2-trifluoroethyl, methoxymethyl, methoxyethyl or ethoxyethyl, $R^7$ represents hydrogen, fluorine, chlorine, amino, cyano, methyl, ethyl, difluoromethyl, chlorodifluoromethyl or trifluoromethyl, $R^8$ represents hydrogen, methyl, ethyl, propyl, isopropyl, tert-butyl, difluoromethyl, chlorodifluoromethyl, trifluoromethylmethoxy, ethoxy, isopropoxy, tert-butoxy, methylthio, ethylthio, propylthio, isopropylthio, difluoromethylthio, chlorodifluoromethylthio, trifluoromethylthio, 3-fluoropropylthio or cyclopropyl, $R^9$ represents hydrogen, methyl, ethyl, propyl, isopropyl, tert-butyl, 1-ethyl-1-methylpropyl, 1,1-dimethylpropyl, difluoromethyl, chlorodifluoromethyl or trifluoromethyl, $R^{10}$ represents hydrogen, methyl ethyl, propyl or isopropyl $R^{11}$ represents hydrogen, methyl, ethyl, propyl, isopropyl tert-butyl 1-ethyl-1-methylpropyl, 1,1-dimethylpropyl, difluoromethyl chlorodifluoromethyl. trifluoromethyl, 1,1-dimethylpropargyl or cyclopropyl, $R^{12}$ represents hydrogen, fluorine, chlorine, cyano or amino, $R^{13}$ represents chlorine, bromine, a group Al—$CHR^{10}R^{14}$ or a group $NR^{10}R^{14}$, $R^{14}$ represents hydrogen, methyl, ethyl, propyl, isopropyl, difluoromethyl, chlorodifluoromethyl, trifluoro-methyl, cyclopropyl, optionally substituted phenyl wherein the substituents are selected from the group consisting of fluorine, chlorine and trifluoromethyl, optionally substituted pyrazolyl wherein the substituents are selected from the group consisting of fluorine, chlorine, methyl and trifluoromethyl, optionally substituted isoxazolyl wherein the substituents are selected from the group consisting of fluorine, chlorine, methyl and trifluoromethyl, optionally substituted thienyl wherein the substituents are selected from the group consisting of fluorine, chlorine, methyl and trifluoromethyl or optionally substituted pyridyl wherein the substituents are selected from the group consisting of fluorine, chlorine, methyl and trifluoromethyl, $R^{15}$ represents fluorine, chlorine or $OR^{16}$, $R^{16}$ represents hydrogen, acetyl or benzoyl, $R^{17}$ and $R^{18}$ each represent independently methyl, ethyl or isopropyl $R^{19}$ and $R^{20}$ each represent independently hydrogen, methyl, ethyl, isopropyl, difluoromethyl, chlorodifluoromethyl, trifluoromethyl or cyclopropyl, $R^{21}$ represents hydrogen, methyl or ethyl, $R^{22}$ represents hydrogen, methyl, ethyl or trifluoromethyl $R^{23}$ represents hydrogen, fluorine, chlorine, cyano, optionally substituted phenyl wherein the substituents are selected from the group consisting of fluorine, chlorine and trifluoromethyl, aminocarbonyl, methylaminocarbonyl or ethylaminocarbonyl, $R^{24}$ represents methyl, ethyl, isopropyl tert-butyl, trifluoromethyl optionally substituted phenyl wherein the substituents are selected from the group consisting of fluorine, chlorine and trifluoromethyl or cyclopropyl, $R^{25}$ represents cyano or aminocarbonyl, $R^{26}$ represents methyl, ethyl, propyl, isopropyl, tert-butyl, 2,2,2-trifluoroethyl, 3-fluoropropyl, cyclopropyl, cyclopentyl, cyclohexyl, 1-methylcyclopropyl, 1-methylcyclopentyl, 1-methylcyclohexyl, 1-cyanocyclopropyl, 1-cyanocyclopentyl, 1-cyanocyclohexyl, 1-ethynylcyclopropyl, 1-ethynylcyclopentyl, 1-ethynylcyclohexyl, 1-cyano-1-methylethyl or 1,1-dimethylpropargyl, $R^{27}$ represents hydrogen, methyl, ethyl, isopropyl, tert-butyl, trifluoromethyl, cyclopropyl, cyclopentyl, methoxy, ethoxy, isopropoxy, 2,2,2-trifluoroethoxy or cyclopropylmethoxy, $R^{28}$ represents hydrogen, fluorine or chlorine, $A^2$ represents oxygen or sulfur, and $A^3$ represents oxygen, sulfur or $CH_2$.

Among the phenylacetylene derivatives of formula (I) according to the invention, more preferred compounds are those wherein X represents hydrogen or fluorine, Y represents hydrogen, hydroxy, fluorine, chlorine, cyano, nitro, methyl, trifluoromethyl, methoxy, ethoxy, isopropoxy, cyclopropoxy, cyclopentyloxy, cyclohexyloxy, difluoromethoxy, chlorodifluoromethoxy, trifluoromethoxy, methoxymethoxy, methylthio, ethylthio, isopropylthio, propylthio, cyclopropylthio, cyclopentylthio, difluoromethylthio, chlorodifluoromethylthio, trifluoromethylthio, methylsulfinyl, methylsulfonyl, isopropylsulfonyl, cyclopropylsulfonyl, cyclopentylsulfonyl, difluoromethylsulfonyl, chlorodifluoromethylsulfonyl, trifluoromethylonyl, methylsulfonyloxy, allyloxy, 2-methylallyloxy, propargyloxy, aminosulfonyl, methylaminosulfonyl, ethylminosulfonyl, a group $COOR^c$, aminocarbonyl, amino, methylsulfonylamino, ethylsulfonylamino, bis(methylsulfonyl)amino, bis(ethylsulfonyl)amino, (acetyl)(ethylsulfonyl)amino, (tert-butylcarbonyl)(methylsulfonyl)amino, (tert-butylcarbonyl)(ethylsulfonyl)amino, 1-(methoxycarbonyl)ethylthio, ethoxycarbonylmethylthio, methoxycarbonylmethylthio, 1-(ethoxycarbonyl)ethylthio, 1-(methoxycarbonyl)ethoxy, ethoxycarbonylmethylthoxy, methoxycarbonylmethoxy, 2-(ethoxycarbonyl)-2-chloroethoxy, ethoxycarbonylmethyl or 2-(ethoxycarbonyl)-2-chloroethyl, R<sup>c</sup> represents hydrogen, methyl, ethyl, propyl, isopropyl, methoxycarbonylmethyl, ethoxycarbonylmethyl, 1-(methoxycarbonyl)ethyl or 1-(ethoxycarbonyl)ethyl, A¹ represents oxygen or sulfur, n is 0 or 1, Z represents hydrogen, fluorine or chlorine, m is 1, R represents hydrogen, fluorine, hydroxymethyl trimethylsilyl, methoxycarbonyl or ethoxycarbonyl, Q represents a heterocyclic group selected from

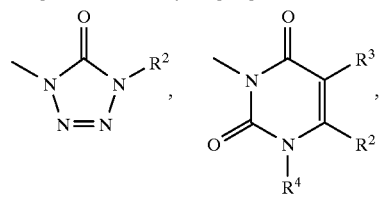

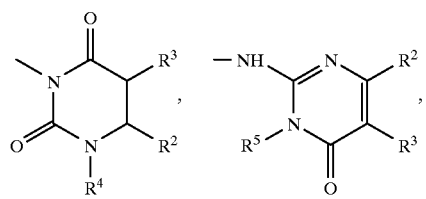

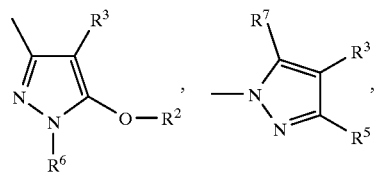

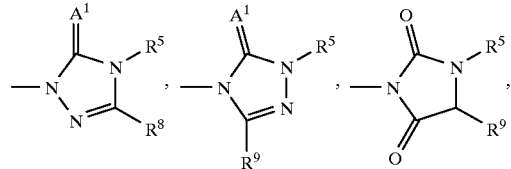

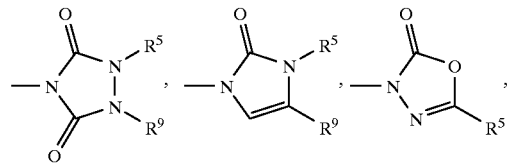

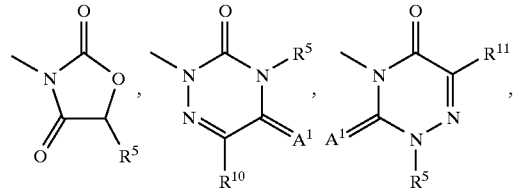

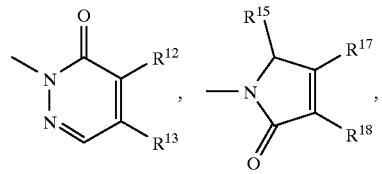

-continued

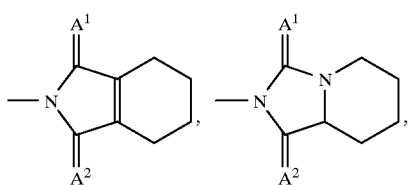

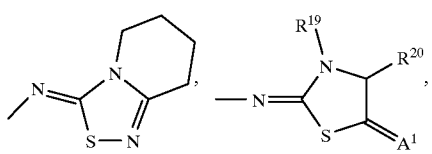

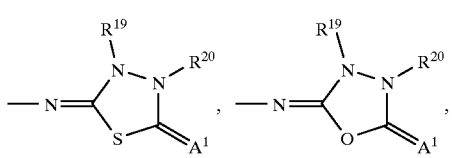

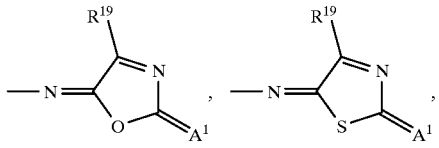

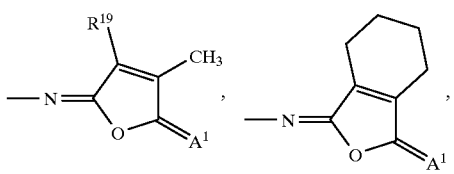

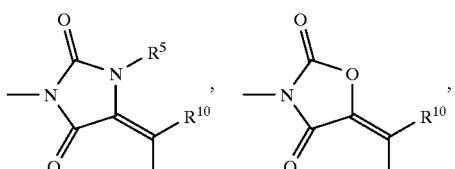

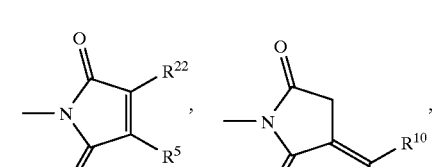

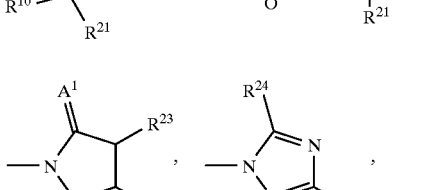

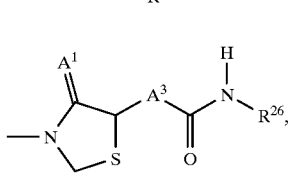

-continued

[Chemical structures shown]

R² represents hydrogen, trifluoromethyl, difluoromethyl, chlorodifluoromethyl, 2,2,2-trifluoro ethyl, 3-fluoropropyl, 3,3,3-trifluoropropyl, 2,2,3,3-tetrafluoropropyl or 1,1,2,3,3,3-hexafluoropropyl, R³ represents hydrogen, cyano, fluorine, chlorine, methyl or ethyl, R⁴ represents hydrogen, amino, methyl or ethyl, R⁵ represents hydrogen, methyl, ethyl, isopropyl, tert-butyl, 1-ethyl-1-methylpropyl, 1,1-dimethylpropyl, chloromethyl, difluoromethyl, dichlorofluoromethyl, trifluoromethyl, 3-fluoropropyl, 1,1-dimethyl-2-chloroethyl, 1,1-dimethyl-2-fluoroethyl, cyclopropyl or 1,1-dimethylpropargyl, R⁶ represents hydrogen, methyl, ethyl, propyl, isopropyl tert-butyl, 2,2,2-trifluoroethyl, methoxymethyl methoxyethyl or ethoxyethyl R⁷ represents hydrogen, fluorine, chlorine, amino, cyano, methyl, ethyl difluoromethyl, chlorodifluoromethyl or trifluoromethyl, R⁸ represents hydrogen, methyl, ethyl, propyl, isopropyl, tert-butyl difluoromethyl, chlorodifluoromethyl, trifluoromethylmethoxy, ethoxy, isopropoxy, tert-butoxy, methylthio, ethylthio, propylthio, isopropylthio, difluoromethylthio, chlorodifluoromethylthio, trifuoromethylthlo, 3-fluoropropylthio or cyclopropyl, R⁹ represents hydrogen, methyl, ethyl, propyl, isopropyl, tert-butyl, 1-ethyl-1-methylpropyl, 1,1-dimethylpropyl, difluoromethyl, chlorodifluoromethyl or trifluoromethyl, R¹⁰ represents hydrogen, methyl, ethyl, propyl or isopropyl, R¹¹ represents hydrogen, methyl, ethyl, propyl isopropyl, tert-butyl, 1-ethyl-1-methylpropyl, 1,1-dimethylpropyl, difluoromethyl, chlorodifluoromethyl, trifluoromethyl, 1,1-dimethylpropargyl or cyclopropyl, R¹² represents hydrogen, fluorine, chlorine, cyano or amino, R¹³ represents chlorine, bromine, a group A1—CHR¹⁰R¹⁴ or a group NR¹⁰R¹⁴, R¹⁴ represents hydrogen, methyl, ethyl, propyl, isopropyl, difluoromethyl, chlorodifluoromethyl, trifluoromethyl, cyclopropyl, optionally substituted phenyl wherein the substituents are selected from the group consisting of fluorine, chlorine and trifluoromethyl, optionally substituted pyrazolyl wherein the substituents are selected from the group consisting of fluorine, chlorine, methyl and trifluoromethyl, optionally substituted isoxazolyl wherein the substituents are selected from the group consisting of fluorine, chlorine, methyl and trifluoromethyl, optionally substituted thienyl wherein the substituents are selected from the group consisting of fluorine, chlorine, methyl and trifluoromethyl or optionally substituted pyridyl wherein the substituents are selected from the group consisting of fluorine, chlorine, methyl and trifluoromethyl, R¹⁵ represents fluorine, chlorine or OR¹⁶, R¹⁶ represents hydrogen, acetyl or benzoyl, R¹⁷ and R¹⁸ each represent independently methyl, ethyl or isopropyl, R¹⁹ and R²⁰ each represent independently hydrogen, methyl ethyl, isopropyl, difluoromethyl, chlorodifluoromethyl, trifluoromethyl or cyclopropyl, R²¹ represents hydrogen, methyl or ethyl, R²² represents hydrogen, methyl, ethyl or trifluoromethyl, R²³ represents hydrogen, fluorine, chlorine, cyano, optionally substituted phenyl wherein the substituents are selected from the group consisting of fluorine, chlorine and trifluoromethyl, aminocarbonyl, methylaminocarbonyl or ethylaminocarbonyl, R²⁴ represents methyl, ethyl, isopropyl, tert-butyl, trifluoromethyl, optionally substituted phenyl wherein the substituents are selected from the group consisting of fluorine, chlorine and trifluoromethyl or cyclopropyl, R²⁵ represents cyano or aminocarbonyl, R²⁶ represents methyl, ethyl, propyl, isopropyl, tert-butyl, 2,2,2-trifluoroethyl, 3-fluoropropyl, cyclopropyl, cyclopentyl, cyclohexyl, 1-methylcyclopropyl, 1-methylcyclopentyl, 1-methylcyclohexyl, 1-cyanocyclopropyl, 1-cyanocyclopentyl, 1-cyanocyclohexyl, 1-ethynylcyclopropyl, 1-ethynylcyclopentyl, 1-ethynylcyclohexyl, 1-cyano-1-methylethyl or 1,1-dimethylpropargyl, R²⁷ represents hydrogen, methyl, ethyl, isopropyl, tert-butyl, trifluoromethyl, cyclopropyl, cyclopentyl methoxy, ethoxy, isopropoxy, 2,2,2-trifluoroethoxy or cyclopropylmethoxy, $R^{28}$ represents hydrogen, fluorine or chlorine, $A^2$ represents oxygen or sulfur, and $A^3$ represents oxygen, sulfur or $CH_2$.

Certain phenylacetylene derivatives of formula (I) according to the invention are listed in the following Table 1.

TABLE 1

| R | X | Y | Zm | $R^2$ |
|---|---|---|----|-------|
| $Si(CH_3)_3$ | F | $OCH_3$ | H | $CHF_2$ |
| $Si(CH_3)_3$ | F | $OCH_3$ | H | $CH_2CH_2CH_2F$ |
| H | F | $OCH_3$ | H | $CHF_2$ |
| H | F | $OCH(CH_3)_2$ | H | $CH_2CH_2CH_2F$ |
| H | F | O-cyclopentyl | H | $CHF_2$ |
| H | F | O-cyclopentyl | H | $CH_2CH_2CH_2F$ |
| H | F | S-cyclopentyl | H | $CH_2CH_2CH_2F$ |
| H | F | $NH_2$ | H | $CH_2CH_2CH_2F$ |
| H | F | $NHSO_2CH_3$ | H | $CH_2CH_2CH_2F$ |
| H | F | $NHSO_2C_2H_5$ | H | $CH_2CH_2CH_2F$ |
| H | F | $NHSO_2CH_3$ | H | $CHF_2$ |
| H | F | $NHSO_2C_2H_5$ | H | $CHF_2$ |
| H | F | $CO_2CH_3$ | H | $CH_2CH_2CH_2F$ |
| H | F | $CO_2CH(CH_3)_2$ | H | $CHF_2$ |
| H | H | $CO_2CH(CH_3)_2$ | H | $CH_2CH_2CH_2F$ |
| $CH_3$ | F | $OCH_3$ | H | $CH_2CH_2CH_2F$ |
| $CO_2C_2H_5$ | F | $OCH(CH_3)_2$ | H | $CHF_2$ |
| H | F | $OCH_2CO_2CH_3$ | H | $CH_2CH_2CH_2F$ |
| H | F | $OCH(CH_3)CO_2C_2H_5$ | H | $CHF_2$ |
| H | F | $SCH_2CO_2CH_3$ | H | $CH_2CH_2CH_2F$ |
| $Si(CH_3)_3$ | F | H | H | $CHF_2$ |
| H | F | H | H | $CH_2CH_2CH_2F$ |
| $Si(CH_3)_3$ | F | H | H | $CH_2CH_2CH_2F$ |
| H | F | $N(SO_2CH_2CH_3)_2$ | H | $CH_2CH_2CH_2F$ |
| $Si(CH_3)_3$ | F | H | H | $CH_2CH_2CH_2F$ |
| H | F | $N(SO_2CH_2CH_3)_2$ | H | $CH_2CH_2CH_2F$ |
| $Si(CH_3)_3$ | F | $N(SO_2CH_2CH_3)_2$ | H | $CH_2CH_2CH_2F$ |
| $Si(CH_3)_3$ | F | $NH_2$ | H | $CH_2CH_2CH_2F$ |
| $Si(CH_3)_3$ | F | $NO_2$ | H | $CH_2CH_2CH_2F$ |

| R | X | Y | Zm | $R^2$ | $R^3$ | $R^4$ |
|---|---|---|----|-------|-------|-------|
| $Si(CH_3)_3$ | F | $OCH_3$ | H | $CF_3$ | H | $CH_3$ |
| H | F | $OCH_3$ | H | $CF_3$ | $CH_3$ | $CH_3$ |
| H | F | $OCH(CH_3)_2$ | H | $CF_3$ | H | $CH_3$ |
| H | F | O-cyclopentyl | H | $CF_3$ | H | $CH_3$ |
| H | H | H | H | $CF_3$ | H | $CH_3$ |
| H | F | H | H | $CF_3$ | H | $CH_3$ |
| H | F | $CO_2CH(CH_3)_2$ | H | $CF_3$ | H | $CH_3$ |
| H | F | $NHSO_2CH_3$ | H | $CF_3$ | $CH_3$ | $CH_3$ |
| H | F | $NHSO_2C_2H_5$ | H | $CF_3$ | H | $CH_3$ |
| H | F | $OCH(CH_3)_2$ | H | $CHF_2$ | H | $CH_3$ |
| H | F | $OCH_2CO_2C_2H_5$ | H | $CF_3$ | H | $CH_3$ |

TABLE 1-continued

| | | | | | | |
|---|---|---|---|---|---|---|
| H | F | OCH$_2$CO$_2$CH$_3$ | H | CF$_3$ | H | CH$_3$ |
| Si(CH$_3$)$_3$ | F | OCH$_2$CO$_2$CH$_3$ | H | CF$_3$ | H | CH$_3$ |
| CH$_3$ | F | OCH$_3$ | H | CF$_3$ | H | CH$_3$ |
| H | F | OCH(CH$_3$)$_2$ | H | CClF$_2$ | H | CH$_3$ |

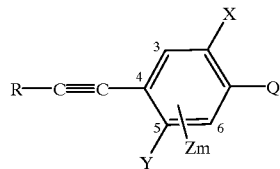

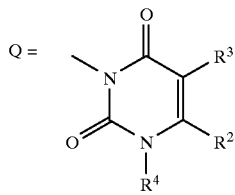

| R | X | Y | Zm | R$^2$ | R$^3$ | R$^4$ |
|---|---|---|---|---|---|---|
| H | F | OCF$_3$ | H | CF$_3$ | H | CH$_3$ |
| H | F | OCH(CH$_3$)$_2$ | H | CF$_3$ | H | NH$_2$ |
| H | F | OCH$_3$ | H | CF$_3$ | H | CH$_3$ |
| Si(CH$_3$)$_3$ | H | H | H | CF$_3$ | H | CH$_3$ |
| Si(CH$_3$)$_3$ | F | O-cyclopentyl | H | CF$_3$ | H | CH$_3$ |
| Si(CH$_3$)$_3$ | F | OC$_2$H$_5$ | H | CF$_3$ | H | CH$_3$ |
| H | F | OC$_2$H$_5$ | H | CF$_3$ | H | CH$_3$ |
| H | Cl | H | H | CF$_3$ | H | CH$_3$ |
| CH$_2$CH$_2$CH$_2$CH$_3$ | Cl | H | H | CF$_3$ | H | CH$_3$ |
| Si(CH$_3$)$_3$ | Cl | H | H | CF$_3$ | H | CH$_3$ |
| H | F | NHSO$_2$CH$_3$ | H | CF$_3$ | H | CH$_3$ |
| C(CH$_3$)$_3$ | Cl | H | H | CF$_3$ | H | CH$_3$ |
| H | F | OSO$_2$CH$_3$ | H | CF$_3$ | H | CH$_3$ |
| H | F | N(SO$_2$CH$_3$)$_2$ | H | CF$_3$ | H | CH$_3$ |
| H | F | NO$_2$ | H | CF$_3$ | H | CH$_3$ |
| H | F | OCH(CH$_3$)$_2$ | H | CF$_3$ | CH$_3$ | CH$_3$ |
| Si(CH$_3$)$_3$ | F | NO$_2$ | H | CF$_3$ | CH$_3$ | CH$_3$ |
| H | F | NO$_2$ | H | CF$_3$ | CH$_3$ | CH$_3$ |
| Si(CH$_3$)$_3$ | F | NH$_2$ | H | CF$_3$ | CH$_3$ | CH$_3$ |
| H | F | NH$_2$ | H | CF$_3$ | CH$_3$ | CH$_3$ |
| H | F | H | H | CF$_3$ | CH$_3$ | CH$_3$ |
| Si(CH$_3$)$_3$ | F | H | H | CF$_3$ | CH$_3$ | CH$_3$ |
| H | H | OCF$_3$ | H | CF$_3$ | H | CH$_3$ |
| Si(CH$_3$)$_3$ | H | OCF$_3$ | H | CF$_3$ | H | CH$_3$ |
| H | F | OCF$_2$CHFCl | H | CF$_3$ | H | CH$_3$ |
| Si(CH$_3$)$_3$ | H | CO$_2$C$_2$H$_5$ | H | CF$_3$ | H | CH$_3$ |
| H | H | CO$_2$C$_2$H$_5$ | H | CF$_3$ | H | CH$_3$ |
| Si(CH$_3$)$_3$ | H | OCH$_2$CH$_2$CH$_3$ | H | CF$_3$ | H | CH$_3$ |
| Si(CH$_3$)$_3$ | F | OCF$_3$ | H | CF$_3$ | H | CH$_3$ |
| Si(CH$_3$)$_3$ | F | NHCOCH$_3$ | H | CF$_3$ | CH$_3$ | CH$_3$ |
| Si(CH$_3$)$_3$ | F | SCH$_3$ | H | CF$_3$ | H | CH$_3$ |
| Si(CH$_3$)$_3$ | F | SC$_2$H$_5$ | H | CF$_3$ | H | CH$_3$ |
| Si(CH$_3$)$_3$ | F | S-cyclopentyl | H | CF$_3$ | H | CH$_3$ |
| H | F | OCF$_3$ | H | CF$_3$ | H | CH$_3$ |
| H | F | NHCOCH$_3$ | H | CF$_3$ | CH$_3$ | CH$_3$ |
| H | F | OCH$_3$ | H | CF$_3$ | H | CH$_3$ |
| H | F | OCH(CH$_3$)CO$_2$C$_2$H$_5$ | H | CF$_3$ | H | CH$_3$ |
| H | F | OCH$_2$CH$_2$CH$_3$ | H | CF$_3$ | H | CH$_3$ |
| H | F | OCH$_2$OCH$_3$ | H | CF$_3$ | H | CH$_3$ |
| H | F | SCH$_3$ | H | CF$_3$ | H | CH$_3$ |
| H | F | SC$_2$H$_5$ | H | CF$_3$ | H | CH$_3$ |
| H | F | S-cyclopentyl | H | CF$_3$ | H | CH$_3$ |
| H | F | SCH(CH$_3$)$_2$ | H | CF$_3$ | H | CH$_3$ |
| H | F | SCH$_3$ | H | CF$_3$ | CH$_3$ | CH$_3$ |
| H | F | SC$_2$H$_5$ | H | CHF$_2$ | H | CH$_3$ |
| H | F | SCH$_2$CH$_2$CH$_3$ | H | CF$_3$ | H | CH$_3$ |
| H | F | SCH$_2$CO$_2$C$_2$H$_5$ | H | CF$_3$ | H | CH$_3$ |
| H | F | SOCH$_3$ | H | CF$_3$ | H | CH$_3$ |
| H | F | SO$_2$CH$_3$ | H | CF$_3$ | H | CH$_3$ |
| H | F | SO$_2$-cyclopentyl | H | CF$_3$ | H | CH$_3$ |
| H | Cl | SCH$_3$ | H | CF$_3$ | H | CH$_3$ |
| H | F | SO$_2$NH$_2$ | H | CF$_3$ | H | CH$_3$ |

TABLE 1-continued

| R | X | Y | Zm | R² | R³ | R⁴ |
|---|---|---|---|---|---|---|
| H | F | SO₂NHCH₃ | H | CF₃ | H | CH₃ |
| H | F | SO₂N(CH₃)₂ | H | CF₃ | H | CH₃ |
| H | F | SO₂-pyrrolidin-1-yl | H | CF₃ | H | CH₃ |
| H | F | NHSO₂CF₃ | H | CF₃ | H | CH₃ |
| H | F | NHSO₂CH₂CF₃ | H | CF₃ | H | CH₃ |
| H | F | N(CH₃)SO₂CH₃ | H | CF₃ | H | CH₃ |
| H | F | N(CH₂CH=CH₂)SO₂C₂H₅ | H | CF₃ | H | CH₃ |
| H | F | N(CH₂CCH)SO₂CH₃ | H | CF₃ | CH₃ | CH₃ |
| H | F | N(COCH₃)SO₂CH₃ | H | CF₃ | H | CH₃ |
| H | F | N(COC(CH₃)₃)SO₂CH₃ | H | CF₃ | H | CH₃ |
| H | F | N(COC(CH₃)₃)SO₂CH₃ | H | CF₃ | CH₃ | CH₃ |
| H | F | NHSO₂CH₃ | H | CF₃ | H | NH₂ |
| H | F | CO₂CH₃ | H | CF₃ | H | CH₃ |
| H | F | CO₂C₂H₅ | H | CF₃ | H | CH₃ |
| H | F | CO₂CH(CH₃)₂ | H | CF₃ | CH₃ | CH₃ |
| H | F | CONH₂ | H | CF₃ | H | CH₃ |
| H | F | CON(CH₃)₂ | H | CF₃ | H | CH₃ |
| H | F | CONHCH₃ | H | CF₃ | H | CH₃ |
| H | F | CO-pyrrolidin-1-yl | H | CF₃ | H | CH₃ |
| H | F | CONH-cyclopropyl | H | CF₃ | H | CH₃ |
| Si(CH₃)₃ | F | 5-OCH(CH₃)CH₂-6 | | CF₃ | H | CH₃ |
| H | F | 5-OCH(CH₃)CH₂-6 | | CF₃ | H | CH₃ |
| Si(CH₃)₃ | F | 5-OCH(CH₃)CH₂-6 | | CF₃ | CH₃ | CH₃ |
| H | F | 5-OCH(CH₃)CH₂-6 | | CF₃ | CH₃ | CH₃ |
| H | F | 5-OCH(CH₂OH)CH₂-6 | | CF₃ | H | CH₃ |
| H | F | 5-OCH(COOH)CH₂-6 | | CF₃ | H | CH₃ |
| H | F | 5-OCH(CO₂CH₃)CH₂-6 | | CF₃ | H | CH₃ |
| H | F | 5-OC(CH₃)₂CH₂-6 | | CF₃ | H | CH₃ |
| H | F | 5-OC(CH₃)(CH₂OH)CH-6 | | CF₃ | H | CH₃ |
| H | F | 5-OC(CH₃)(COOH)CH₂-6 | | CF₃ | H | CH₃ |
| H | F | 5-OC(CH₃)(CO₂C₂H₅)CH₂-6 | | CF₃ | H | CH₃ |
| H | F | 5-OC(CH₃)(CH₂OCH₃)CH₂-6 | | CF₃ | H | CH₃ |
| H | H | 5-OCH(CH₃)CH₂-6 | | CF₃ | H | CH₃ |
| H | F | 5-OC(CH₃)=CH-6 | | CF₃ | H | CH₃ |
| H | F | SO₂C₂H₅ | H | CF₃ | H | CH₃ |
| Si(CH₃)₃ | F | H | H | CF₃ | H | CH₃ |
| Si(CH₃)₃ | F | NO₂ | H | CF₃ | H | CH₃ |
| Si(CH₃)₃ | F | N(COC(CH₃)₃)SO₂CH₃ | H | CF₃ | H | CH₃ |
| H | F | N(COC(CH₃)₃)SO₂C₂H₅ | H | CF₃ | H | CH₃ |
| H | F | N(COCH₃)SO₂C₂H₅ | H | CF₃ | H | CH₃ |
| Si(CH₃)₃ | F | NHSO₂C₂H₅ | H | CF₃ | H | CH₃ |
| H | F | OCH₂CH(CH₃) | H | CF₃ | H | CH₃ |
| H | F | OH | H | CF₃ | H | CH₃ |
| H | F | O-cyclobutyl | H | CF₃ | H | CH₃ |
| CH₂OH | F | OCH₃ | H | CF₃ | H | CH₃ |
| CH₂CH₂CH₃ | H | H | H | CF₃ | H | CH₃ |
| H | F | OCH₂CH₂CH₂CH₃ | H | CF₃ | H | CH₃ |
| H | F | OCH₂CH=CH₂ | H | CF₃ | H | CH₃ |
| H | F | OCH₂C≡CH | H | CF₃ | H | CH₃ |
| H | F | OCH₂OCH₃ | H | CF₃ | H | CH₃ |
| Si(CH₃)₃ | F | OCH₂OCH₃ | H | CF₃ | H | CH₃ |
| Si(CH₃)₃ | F | OH | H | CF₃ | H | CH₃ |
| H | F | OCH₂C(CH₃)=CH₂ | H | CF₃ | H | CH₃ |
| H | F | OCH₂CH₂F | H | CF₃ | H | CH₃ |
| H | F | OCH₂CH₂CH₂F | H | CF₃ | H | CH₃ |
| H | F | OCH(CH₃)₂ | H | CF₃ | H | CH₃ |
| H | F | OCH₂CH₂CH₂CH₃ | H | CF₃ | H | CH₃ |

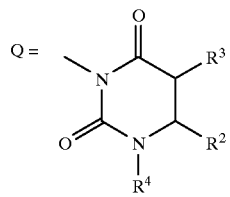

Q =

| R | X | Y | Zm | R² | R³ | R⁴ |
|---|---|---|---|---|---|---|
| Si(CH₃)₃ | F | OCH₃ | H | CF₃ | H | CH₃ |
| H | F | OCH₃ | H | CF₃ | CH₃ | CH₃ |
| H | F | OCH(CH₃)₂ | H | CF₃ | H | CH₃ |
| H | F | O-cyclopropyl | H | CF₃ | H | CH₃ |
| H | F | NHSO₂CH₃ | H | CF₃ | H | CH₃ |

TABLE 1-continued

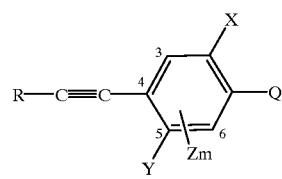

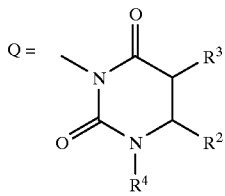

| R | X | Y | Zm | $R^2$ | $R^3$ | $R^4$ |
|---|---|---|----|-------|-------|-------|
| H | F | $NHSO_2C_2H_5$ | H | $CF_3$ | H | $CH_3$ |
| H | F | $NHSO_2CH_3$ | H | $CF_3$ | $CH_3$ | $CH_3$ |
| H | F | $NHSO_2C_2H_5$ | H | $CF_3$ | $CH_3$ | $CH_3$ |
| H | F | $CO_2CH(CH_3)_2$ | H | $CF_3$ | H | $CH_3$ |
| H | F | $OCF_3$ | H | $CHF_2$ | H | $CH_3$ |

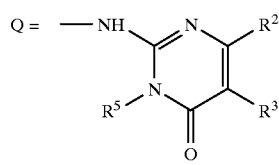

| R | X | Y | Zm | $R^2$ | $R^3$ | $R^5$ |
|---|---|---|----|-------|-------|-------|
| $Si(CH_3)_3$ | F | H | H | $CF_3$ | H | $CH_3$ |
| H | F | H | H | $CF_3$ | $CH_3$ | $CH_3$ |
| H | F | H | H | $CHF_2$ | H | $CH_3$ |
| H | F | H | H | $CClF_2$ | H | $CH_3$ |
| H | F | $OCH_3$ | H | $CF_3$ | H | $CH_3$ |
| H | F | $OC_2H_5$ | H | $CF_3$ | $CH_3$ | $CH_3$ |
| H | F | $OCH(CH_3)_2$ | H | $CF_3$ | H | $CH_3$ |
| H | F | O-cyclopropyl | H | $CF_3$ | H | $CH_3$ |
| H | F | $NHSO_2CH_3$ | H | $CF_3$ | $CH_3$ | $CH_3$ |
| H | F | $NHSO_2C_2H_5$ | H | $CF_3$ | H | $CH_3$ |
| H | F | $CO_2CH(CH_3)_2$ | H | $CF_3$ | H | $CH_3$ |

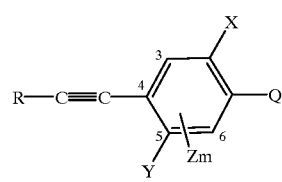

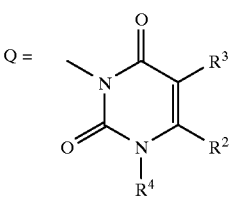

| R | X | Y | Zm | $R^2$ | $R^3$ | $R^5$ |
|---|---|---|----|-------|-------|-------|
| H | F | $OCH_2CO_2C_2H_5$ | H | $CF_3$ | H | $CH_3$ |
| H | F | $OCH(CH_3)CO_2CH_3$ | H | $CF_3$ | H | $CH_3$ |
| H | F | S-cyclopropyl | H | $CF_3$ | H | $CH_3$ |
| H | F | $SCH_2CO_2CH_3$ | H | $CF_3$ | H | $CH_3$ |

TABLE 1-continued

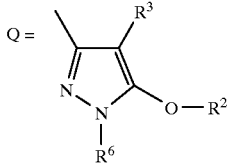

| R | X | Y | Zm | R² | R³ | R⁶ |
|---|---|---|----|----|----|----|
| Si(CH₃)₃ | F | H | H | CHF₂ | H | CH₃ |
| H | F | OCH₃ | H | CHF₂ | Cl | CH₃ |
| H | F | OCH(CH₃)₂ | H | CHF₂ | CH₃ | CH₃ |
| H | F | OCH(CH₃)₂ | H | CHF₂ | H | CH₃ |
| H | F | O-cyclopropyl | H | CHF₂ | H | CH₃ |
| H | F | OCH₃ | H | CH₂CH₂CH₂F | H | CH(CH₃)₂ |
| H | F | OCH(CH₃)₂ | H | CHF₂ | H | C₂H₅ |
| H | F | O-cyclopropyl | H | CHF₂ | H | C(CH₃)₃ |
| H | F | NHSO₂CH₃ | H | CHF₂ | CH₃ | CH₃ |
| H | F | NHSO₂C₂H₅ | H | CHF₂ | Cl | CH₃ |
| H | F | S-cyclopentyl | H | CHF₂ | H | CH₃ |
| H | F | OCH₂CO₂C₂H₅ | H | CHF₂ | Cl | CH₃ |

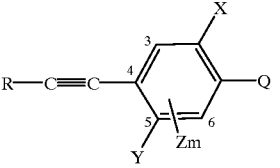

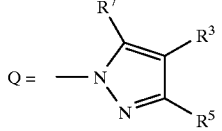

| R | X | Y | Zm | R³ | R⁵ | R⁷ |
|---|---|---|----|----|----|----|
| Si(CH₃)₃ | F | OCH₃ | H | H | CH₃ | CN |
| H | F | OCH(CH₃)₂ | H | Cl | CF₃ | CN |
| H | F | O-cyclopentyl | H | CH₃ | CHF₂ | Cl |
| H | F | OCH₃ | H | H | CF₃ | Cl |
| H | F | OCH(CH₃)₂ | H | Cl | CF₃ | CF₃ |
| H | F | O-cyclopentyl | H | CN | CF₃ | CF₃ |
| H | F | OCH(CH₃)₂ | H | CN | H | NH₂ |
| H | F | OCH₂CO₂C₂H₅ | H | CN | H | NH₂ |
| Si(CH₃)₃ | F | OCH₃ | H | CN | H | NH₂ |
| H | F | OCH₃ | H | CN | H | NH₂ |
| H | F | OC₂H₅ | H | SCH₃ | H | NH₂ |

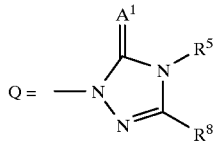

| R | X | Y | Zm | R⁵ | R⁸ | A¹ |
|---|---|---|----|----|----|----|
| Si(CH₃)₃ | F | OCH₃ | H | CHF₂ | CH₃ | O |
| H | F | OCH₃ | H | CH₂CH₂CH₂F | CH₃ | O |
| H | F | OCH(CH₃)₂ | H | C(CH₃)₃ | SCH₃ | O |
| H | F | O-cyclopentyl | H | CH₂CH₂CH₂F | SCH(CH₃)₂ | O |
| H | F | NHSO₂CH₃ | H | CH₂CH₂CH₂F | OCH(CH₃)₂ | O |
| H | F | OCH₃ | H | CH(CH₃)₂ | CF₃ | S |
| H | F | O-cyclopentyl | H | cyclopentyl | CH(CH₃)₂ | O |

TABLE 1-continued

Structure: R—C≡C— attached to benzene ring with X at position facing, Q, Y at position 5, Zm at position 6, positions labeled 3,4,5,6.

$$Q = -N\underset{N}{\overset{A^1}{\underset{\|}{\bigvee}}}\overset{R^5}{\underset{R^8}{N}}$$

(1,2,4-triazole ring with A¹ double bond, R⁵ on N4, R⁸ on C3)

| R | X | Y | Zm | R⁵ | R⁸ | A¹ |
|---|---|---|---|---|---|---|
| H | F | $CH_2CO_2C_2H_5$ | H | $CH_2CH_2CH_2F$ | $C(CH_3)_3$ | O |
| H | F | $NHSO_2C_2H_5$ | H | $CH_2CH_2CH_2F$ | $CH_3$ | O |
| H | F | O-cyclopentyl | H | $CHF_2$ | $CH_3$ | O |
| H | F | $OCH_3$ | H | $CHF_2$ | $CH_3$ | O |
| H | F | $OCH(CH_3)_2$ | H | $CHF_2$ | $CH_3$ | O |
| H | F | $CH_2CO_2C_2H_5$ | H | $CHF_2$ | $CH_3$ | O |
| H | F | $OCH_2CO_2C_2H_5$ | H | $CHF_2$ | $CH_3$ | O |
| H | F | $SCH(CH_3)CO_2CH_3$ | H | $CHF_2$ | $CH_3$ | O |
| H | F | $NHSO_2CH_3$ | H | $CHF_2$ | $CH_3$ | O |
| H | F | $NHSO_2C_2H_5$ | H | $CHF_2$ | $CH_3$ | O |
| H | F | $CO_2CH(CH_3)_2$ | H | $CHF_2$ | $CH_3$ | O |
| H | F | $CH_2CHCl(CO_2C_2H_5)$ | H | $CHF_2$ | $CH_3$ | O |

$$Q = -N\underset{N}{\overset{A^1}{\underset{\|}{\bigvee}}}\overset{R^5}{\underset{R^9}{N}}$$

(1,2,4-triazole ring with A¹ on C3, R⁵ on N2, R⁹ on C5)

| R | X | Y | Zm | R⁵ | R⁹ | A¹ |
|---|---|---|---|---|---|---|
| $Si(CH_3)_3$ | F | $OCH_3$ | H | $CH_2CH_2CH_2F$ | $CH_3$ | O |
| H | F | $OCH_3$ | H | $CH_2CH_2CH_2F$ | $CH(CH_3)_2$ | O |
| H | F | $OCH(CH_3)_2$ | H | $CH_2CH_2CH_2F$ | $CH_3$ | O |
| H | F | O-cyclopentyl | H | $CH_2CH_2CH_2F$ | $CH_3$ | O |
| H | F | $OCH_3$ | H | $CHF_2$ | $CF_3$ | O |
| H | F | $OCH(CH_3)_2$ | H | $CHF_2$ | $CH(CH_3)_2$ | O |

Structure: R—C≡C— attached to benzene ring with X, Q, Y, Zm substituents (positions 3,4,5,6).

$$Q = -N\underset{N}{\overset{A^1}{\underset{\|}{\bigvee}}}\overset{R^5}{\underset{R^9}{N}}$$

| R | X | Y | Zm | R⁵ | R⁹ | A¹ |
|---|---|---|---|---|---|---|
| H | F | O-cyclopentyl | H | $CH_2CH_2CH_2F$ | $C(CH_3)_3$ | O |
| H | F | $OCH(CH_3)_2$ | H | $CH_2CH_2CH_2F$ | $CF_3$ | S |
| H | F | $NHSO_2CH_3$ | H | $CHF_2$ | $CH_3$ | O |
| H | F | $NHSO_2C_2H_5$ | H | $CH_2CH_2CH_2F$ | $CH(CH_3)_2$ | O |
| H | F | $CO_2CH(CH_3)_2$ | H | $CHF_2$ | $CH_3$ | O |
| H | F | $OCH_2CO_2C_2H_5$ | H | $CH_2CH_2CH_2F$ | $C_2H_5$ | O |
| H | F | $OCH_3$ | H | cyclopropyl | $CF_3$ | O |

TABLE 1-continued

| | | | | | | |
|---|---|---|---|---|---|---|
| H | F | SCH(CH$_3$)CO$_2$CH$_3$ | H | CH$_2$CH$_2$CH$_2$F | CH$_3$ | O |
| H | H | H | 3,6-Cl$_2$ | CH$_3$ | CF$_3$ | S |
| H | H | H | 3,6-Cl$_2$ | CH$_3$ | CF$_3$ | O |

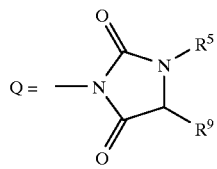

| R | X | Y | Zm | R$^5$ | R$^9$ |
|---|---|---|---|---|---|
| Si(CH$_3$)$_3$ | F | OCH$_3$ | H | CHF$_2$ | H |
| H | F | OCH(CH$_3$)$_2$ | H | CH$_2$CH$_2$CH$_2$F | CH$_3$ |
| H | F | O-cyclopentyl | H | CHF$_2$ | CH(CH$_3$)$_2$ |
| H | F | OCH$_3$ | H | CH$_2$CH$_2$CH$_2$F | C(CH$_3$)$_3$ |
| H | F | S-cyclopentyl | H | CHF$_2$ | CH$_3$ |

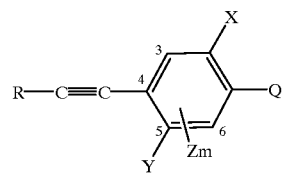

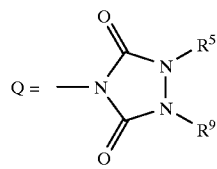

| R | X | Y | Zm | R$^5$ | R$^9$ |
|---|---|---|---|---|---|
| H | F | OCH(CH$_3$)$_2$ | H | CHF$_2$ | CH$_3$ |
| H | F | O-cyclopentyl | H | CH$_2$CH$_2$CH$_2$F | CH$_3$ |
| H | F | NHSO$_2$CH$_3$ | H | CHF$_2$ | CH$_3$ |
| H | F | NHSO$_2$C$_2$H$_5$ | H | CH$_2$CH$_2$CH$_2$F | CH$_3$ |
| H | F | S—CH(CH$_3$)$_2$ | H | CH$_2$CH$_2$CH$_2$F | CH$_3$ |
| H | F | CH$_2$CO$_2$C$_2$H$_5$ | H | CH$_2$CH$_2$CH$_2$F | CH$_3$ |
| H | F | SCH(CH$_3$)CO$_2$CH$_3$ | H | CHF$_2$ | CHF$_2$ |

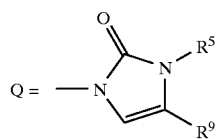

| R | X | Y | Zm | R$^5$ | R$^9$ |
|---|---|---|---|---|---|
| Si(CH$_3$)$_3$ | H | OCH$_3$ | H | CHF$_2$ | CH$_3$ |
| H | F | OCH(CH$_3$)$_2$ | H | CH$_2$CH$_2$CH$_2$F | H |
| H | F | OCH(CH$_3$)$_2$ | H | CHF$_2$ | H |
| H | F | O-cyclopentyl | H | CH$_2$CH$_2$CH$_2$F | C$_2$H$_5$ |
| H | F | NHSO$_2$CH$_3$ | H | CHF$_2$ | H |
| H | F | NHSO$_2$C$_2$H$_5$ | H | CH$_2$CH$_2$CH$_2$F | CH$_3$ |
| H | F | CO$_2$CH(CH$_3$)$_2$ | H | CH$_2$CH$_2$CH$_2$F | H |
| H | F | OCH$_2$CO$_2$C$_2$H$_5$ | H | CHF$_2$ | H |
| H | F | SCH(CH$_3$)CO$_2$CH$_3$ | H | CH$_2$CH$_2$CH$_2$F | H |

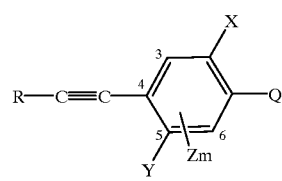

TABLE 1-continued

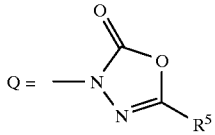

| R | X | Y | Zm | R⁵ |
|---|---|---|---|---|
| Si(CH₃)₃ | H | OCH(CH₃)₂ | H | C(CH₃)₃ |
| H | F | OCH₃ | H | C(CH₃)₃ |
| H | F | OCH(CH₃)₂ | H | CH(CH₃)₂ |
| H | F | OCH(CH₃)₂ | H | CF₃ |
| H | F | O-cyclopentyl | H | C(CH₃)₃ |
| H | F | NHSO₂C₂H₅ | H | cyclopentyl |
| H | F | NHSO₂CH₃ | H | C(CH₃)₃ |
| H | F | NHSO₂C₂H₅ | H | C(CH₃)₃ |
| H | F | OCH₂CO₂C₂H₅ | H | C(CH₃)₃ |
| Si(CH₃)₃ | F | OCH₃ | H | C(CH₃)₃ |

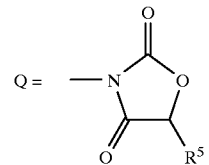

| R | X | Y | Zm | R⁵ |
|---|---|---|---|---|
| Si(CH₃)₃ | H | OCH₃ | H | CH₃ |
| H | F | OCH(CH₃)₂ | H | CH₃ |
| H | F | O-cyclopentyl | H | CH(CH₃)₂ |
| H | F | OCH₂CO₂C₂H₅ | H | CF₃ |
| H | F | NHSO₂CH₃ | H | C(CH₃)₃ |
| H | F | NHSO₂C₂H₅ | H | C(CH₃)₃ |
| H | F | NHSO₂CH₃ | H | CH₃ |
| H | F | NHSO₂C₂H₅ | H | CF₃ |
| H | F | O-cyclopentyl | H | C(CH₃)₃ |

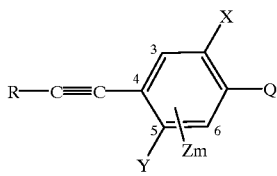

| R | X | Y | Zm | R⁵ | R¹⁰ | A¹ |
|---|---|---|---|---|---|---|
| Si(CH₃)₃ | H | OCH₃ | H | CH₃ | H | O |
| H | F | OCH(CH₃)₂ | H | CH₃ | H | O |
| H | F | O-cyclopentyl | H | CH₃ | H | S |
| H | F | O-cyclopentyl | H | CH₂CH₂CH₂F | H | O |
| H | F | OCH(CH₃)₂ | H | CHF₂ | CH₃ | O |
| H | F | NHSO₂C₂H₅ | H | CH₂CH₂CH₂F | CH₃ | O |
| H | F | OCH₂CO₂C₂H₅ | H | CH₃ | H | O |
| H | F | NHSO₂C₂H₅ | H | CH₃ | H | O |
| H | F | OCH₂OCH₃ | H | CH₃ | H | O |
| H | F | OCH₂SCH₃ | H | CH₂F | H | O |
| H | F | SCH₂OCH₃ | H | CH₃ | H | O |

TABLE 1-continued

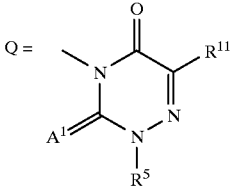

| R | X | Y | Zm | R⁵ | R¹¹ | A¹ |
|---|---|---|---|---|---|---|
| Si(CH₃)₃ | H | OCH₃ | H | CH₃ | C(CH₃)₃ | O |
| H | F | OCH(CH₃)₂ | H | CH₃ | cyclopropyl | O |
| H | F | O-cyclopentyl | H | CH(CH₃)₂ | CF₃ | O |
| H | F | NHSO₂CH₃ | H | CH₃ | cyclopropyl | S |
| H | F | NHSO₂C₂H₅ | H | C₂H₅ | C(CH₃)₃ | O |
| H | F | NHSO₂C₂H₅ | H | CH₃ | C(CH₃)₃ | O |

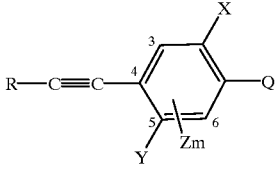

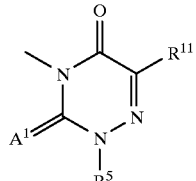

| R | X | Y | Zm | R⁵ | R¹¹ | A¹ |
|---|---|---|---|---|---|---|
| H | F | OCH₂CO₂C₂H₅ | H | CH₃ | cyclopropyl | O |
| H | F | OCH₃ | H | H | CH₃ | O |
| H | F | O-cyclopentyl | H | H | cyclopropyl | O |

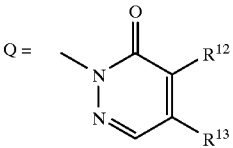

| R | X | Y | Zm | R¹² | R¹³ |
|---|---|---|---|---|---|
| Si(CH₃)₃ | F | OCH₃ | H | Cl | O-cyclopropyl |
| H | F | OCH₃ | H | F | NHCH₃ |
| H | F | OCH(CH₃)₂ | H | Cl | NHCH₃ |
| H | F | O-cyclopentyl | H | Cl | NHCH₃ |
| H | F | OCH₃ | H | Cl | OCH₂CF₃ |
| H | F | OCH₃ | H | Cl | NH₂ |
| H | F | OCH(CH₃)₂ | H | Cl | 2,6-difluorophenyl-methoxy |
| H | F | O-cyclopentyl | H | Cl | 3-trifluoromethylpheyl-methoxy |
| H | F | OCH₃ | H | Cl | 5-trifluoromethylisoxazol-3-yl-methoxy |
| H | F | O-cyclopentyl | H | Cl | 4-chloro-3-trifluromethyl-1-methylpyrazole-4-yl-methoxy |

TABLE 1-continued
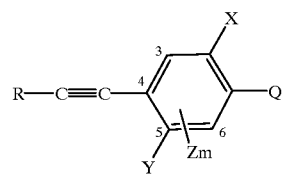
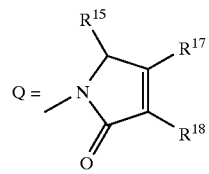
| R | X | Y | Zm | R15 | R17 | R18 |
|---|---|---|----|-----|-----|-----|
| Si(CH3)3 | H | OCH3 | H | OH | CH3 | CH3 |
| H | F | OCH3 | H | Cl | CH3 | CH3 |
| H | F | OCH(CH3)2 | H | OCOCH3 | CH3 | CH3 |
| H | F | O-cyclopentyl | H | OH | CH3 | CH3 |
| H | F | NHSO2CH3 | H | OH | CH3 | CH3 |
| H | F | NHSO2C2H5 | H | OH | CH3 | CH3 |
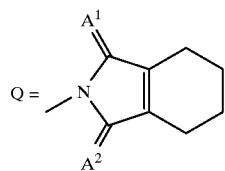
| R | X | Y | Zm | A1 | A2 |
|---|---|---|----|----|----|
| Si(CH3)3 | F | OCH3 | H | O | O |
| H | F | OCH3 | H | O | O |
| H | F | OCH(CH3)2 | H | O | O |
| H | F | NHSO2C2H5 | H | O | O |
| H | F | O-cyclopentyl | H | O | O |
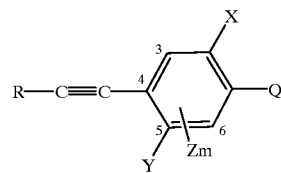
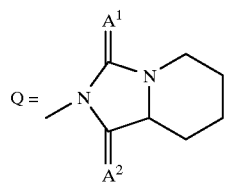
| R | X | Y | Zm | A1 | A2 |
|---|---|---|----|----|----|
| H | F | O-cyclopentyl | H | S | O |
| H | F | NHSO2C2H5 | H | O | O |
| H | F | O-cyclopentyl | H | O | O |
| H | F | NHSO2CH3 | H | S | O |

TABLE 1-continued
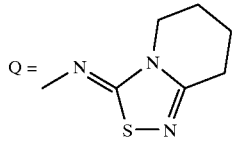
| R | X | Y | Zm |
|---|---|---|---|
| H | F | OCH₃ | H |
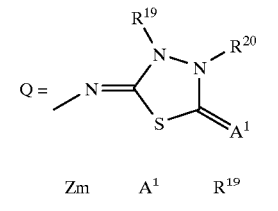
| R | X | Y | Zm | A¹ | R¹⁹ | R²⁰ |
|---|---|---|---|---|---|---|
| Si(CH₃)₃ | F | OCH₃ | H | O | CHF₂ | CH₃ |
| H | F | NHSO₂CH₃ | H | O | CHF₂ | CH₃ |
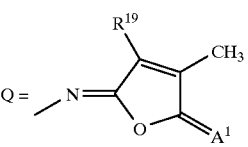
| R | X | Y | Zm | A¹ | R¹⁹ | R²⁰ |
|---|---|---|---|---|---|---|
| H | F | OCH₃ | H | O | CH₂CH₂CH₂F | CH(CH₃)₂ |
| R | X | Y | Zm | A¹ | R¹⁹ | R²⁰ |
|---|---|---|---|---|---|---|
| H | F | CH(CH₃)₂ | H | O | CHF₂ | cyclopropyl |
| H | F | SCH₃ | H | O | CH₃ | CH₃ |
| R | X | Y | Zm | A¹ | R¹⁹ |
|---|---|---|---|---|---|
| H | F | NHSO₂CH₃ | H | O | CH₃ |

TABLE 1-continued

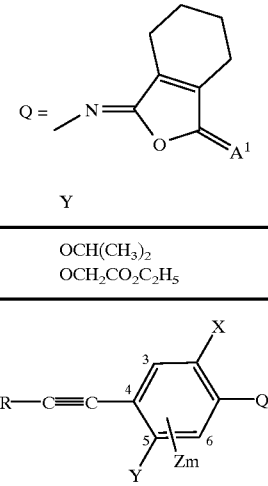

| R | X | Y | Zm | A¹ |
|---|---|---|---|---|
| H | F | OCH(CH₃)₂ | H | O |
| H | F | OCH₂CO₂C₂H₅ | H | O |

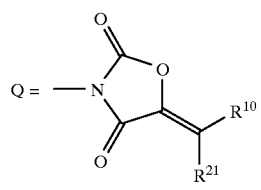

| R | X | Y | Zm | R⁵ | R¹⁰ | R²¹ |
|---|---|---|---|---|---|---|
| Si(CH₃)₃ | H | OCH(CH₃)₂ | H | CHF₂ | CH₃ | CH₃ |
| H | F | OCH₃ | H | CHF₂ | H | H |
| H | F | OCH(CH₃)₂ | H | CH₂CH₂CH₂F | CH₃ | CH₃ |
| H | F | O-cyclopentyl | H | CH₃ | CH₃ | CH₃ |
| H | F | NHSO₂CH₃ | H | CHF₂ | CH₃ | CH₃ |
| H | F | NHSO₂C₂H₅ | H | CH₂CH₂CH₂F | CH₃ | CH₃ |
| H | F | NHSO₂C₂H₅ | H | CHF₂ | CH₃ | CH₃ |
| H | F | OCH₂CO₂C₂H₅ | H | CHF₂ | CH₃ | CH₃ |
| H | F | OCH₂CHClCO₂C₂H₅ | H | CHF₂ | CH₃ | CH₃ |
| H | F | S-cyclopentyl | H | CHF₂ | H | H |

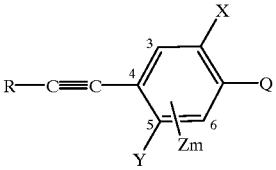

| R | X | Y | Zm | R¹⁰ | R²¹ |
|---|---|---|---|---|---|
| Si(CH₃)₃ | H | OCH₃ | H | H | CH₃ |
| H | F | OCH₃ | H | H | H |
| H | F | OCH₃ | H | CH₃ | CH₃ |
| H | F | OCH(CH₃)₂ | H | CH₃ | CH₃ |
| H | F | O-cyclopentyl | H | CH₃ | CH₃ |
| H | F | NHSO₂CH₃ | H | CH₃ | CH₃ |

TABLE 1-continued

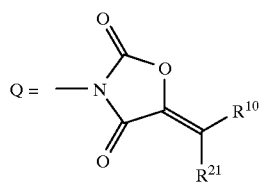

| R | X | Y | Zm | $R^{10}$ | $R^{21}$ |
|---|---|---|---|---|---|
| H | F | $NHSO_2C_2H_5$ | H | $CH_3$ | $CH_3$ |
| H | F | $OCH_2CO_2C_2H_5$ | H | $CH_3$ | $CH_3$ |
| H | F | $OCH_2CHClCO_2C_2H_5$ | H | $CH_3$ | $CH_3$ |
| H | F | S-cyclopropyl | H | $CH_3$ | $CH_3$ |

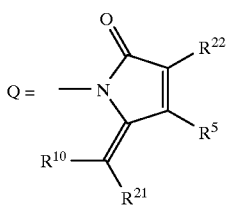

| R | X | Y | Zm | $R^{15}$ | $R^{10}$ | $R^{21}$ | $R^{22}$ |
|---|---|---|---|---|---|---|---|
| $Si(CH_3)_3$ | F | $OCH_3$ | H | H | $CH_3$ | $CH_3$ | $CH(CH_3)_2$ |
| H | F | $OCH(CH_3)_2$ | H | H | $CH_3$ | $CH_3$ | $CF_3$ |
| H | F | O-cyclopentyl | H | $CH_3$ | $CH_3$ | $CH_3$ | H |
| H | F | $OCH_3$ | H | H | $CH_3$ | $CH_3$ | H |
| H | F | $OCH(CH_3)_2$ | H | H | $CH_3$ | $CH_3$ | H |
| H | F | O-cyclopentyl | H | H | $CH_3$ | $CH_3$ | H |
| H | F | $NHSO_2CH_3$ | H | H | $CH_3$ | $CH_3$ | H |
| H | F | $NHSO_2C_2H_5$ | H | H | $CH_3$ | $CH_3$ | H |
| H | F | $OCH_2CO_2C_2H_5$ | H | H | $CH_3$ | $CH_3$ | H |
| H | F | $OCH_2CHClCO_2C_2H_5$ | H | H | $CH_3$ | $CH_3$ | H |

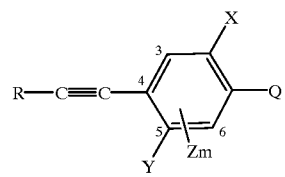

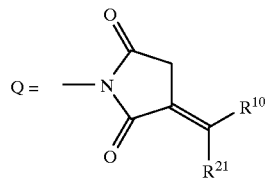

| R | X | Y | Zm | $R^{10}$ | $R^{21}$ |
|---|---|---|---|---|---|
| $Si(CH_3)_3$ | H | $OCH_3$ | H | $CH_3$ | $CH_3$ |
| H | F | $OCH_3$ | H | $CH_3$ | $CH_3$ |
| H | F | $OCH(CH_3)_2$ | H | $CH_3$ | $CH_3$ |
| H | F | O-cyclopentyl | H | $CH_3$ | $CH_3$ |
| H | F | $NHSO_2CH_3$ | H | $CH_3$ | $CH_3$ |
| H | F | $NHSO_2C_2H_5$ | H | $CH_3$ | $CH_3$ |
| H | F | $OCH_2CO_2C_2H_5$ | H | $CH_3$ | $CH_3$ |
| H | F | $OCH_2CHClCO_2C_2H_5$ | H | $CH_3$ | $CH_3$ |
| H | F | S-cyclopentyl | H | $CH_3$ | $CH_3$ |
| H | F | S-cyclopropyl | H | $CH_3$ | $CH_3$ |

TABLE 1-continued

Q = [pyrrolidine structure with A¹=, R²³, R⁵, N]

| R | X | Y | Zm | A¹ | R⁵ | R²³ |
|---|---|---|---|---|---|---|
| Si(CH₃)₃ | F | OCH₃ | H | O | CH₂Cl | Cl |
| H | F | OCH₃ | H | O | CH₂Cl | Cl |
| H | F | OCH(CH₃)₂ | H | O | CH₂Cl | Cl |
| H | F | O-cyclopentyl | H | O | CH₂Cl | Cl |
| H | F | NHSO₂CH₃ | H | O | CH₂Cl | Cl |
| H | F | NHSO₂C₂H₅ | H | O | CH₂Cl | Cl |
| H | F | OCH₃ | H | O | C₂H₅ | 3-fluorophenyl |

Q = [succinimide with =CR¹⁰R²¹ substituent]

Q = [pyrrolidine structure with A¹=, R²³, R⁵, N]

| R | X | Y | Zm | A¹ | R⁵ | R²³ |
|---|---|---|---|---|---|---|
| H | F | OCH(CH₃)₂ | H | O | CH₂Cl | 3,5-difluorophenyl |
| H | F | O-cyclopentyl | H | O | C₂H₅ | 3-chlorophenyl |
| H | F | O-cyclopentyl | H | O | CH₂Cl | CONHC₂H₅ |
| H | F | OCH₃ | H | O | C₂H₅ | CONHC₂H₅ |
| H | F | OCH(CH₃)₂ | H | O | C₂H₅ | CONHC₂H₅ |
| H | F | O-cyclopentyl | H | O | C₂H₅ | CONHC₂H₅ |
| H | F | NHSO₂CH₃ | H | O | C₂H₅ | 3-trifluoromethylphenyl |
| H | F | NHSO₂C₂H₅ | H | O | C₂H₅ | 3-fluorophenyl |
| H | F | OCH(CH₃)₂ | H | S | C₂H₅ | 3-fluorophenyl |
| H | F | O-cyclopentyl | H | S | C₂H₅ | 3,5-difluorophenyl |

Q = [1,2,4-triazole with R²⁴, R²⁵]

| R | X | Y | Zm | R²⁴ | R²⁵ |
|---|---|---|---|---|---|
| Si(CH₃)₃ | H | OCH₃ | H | phenyl | CONH₂ |
| H | F | OCH₃ | H | 2-fluorophenyl | CONH₂ |
| H | F | OCH(CH₃)₂ | H | phenyl | CONH₂ |
| H | F | O-cyclopentyl | H | 2,6-difluorophenyl | CONH₂ |
| H | F | NHSO₂CH₃ | H | 3-fluorophenyl | CONH₂ |
| H | F | NHSO₂C₂H₅ | H | fluorophenyl | CONH₂ |
| H | F | OCH₂CO₂C₂H₅ | H | 2-trifluorophenylmethylphenyl | CONH₂ |
| H | F | S-cyclopentyl | H | 2,4-difluorophenyl | CONH₂ |

TABLE 1-continued

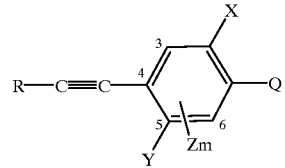

| R | X | Y | Zm | A¹ | A² | R²⁶ |
|---|---|---|----|----|----|-----|
| Si(CH₃)₃ | F | OCH₃ | H | O | O | C(CH₃)₃ |
| H | F | OCH₃ | H | O | O | C(CH₃)₃ |
| H | F | OCH(CH₃)₂ | H | O | O | C(CH₃)₃ |
| H | F | O-cyclopentyl | H | O | O | C(CH₃)₃ |
| H | F | OCH₃ | H | O | O | 1-acetyl-cyclopentyl |
| H | F | OCH(CH₃)₂ | H | O | O | 1-cyanoisopropyl |
| H | F | O-cyclopentyl | H | O | O | 1-cyanocylohexyl |
| H | F | NHSO₂CH₃ | H | O | O | 1-methylcyclohexyl |
| H | F | NHSO₂C₂H₅ | H | O | O | C(CH₃)₃ |
| H | F | O-cyclopentyl | H | O | O | CH₂CH₂CH₂F |

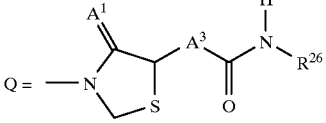

| R | X | Y | Zm | A¹ | A³ | R²⁶ |
|---|---|---|----|----|----|-----|
| H | F | OCH(CH₃)₂ | H | S | O | C(CH₃)₃ |
| H | F | O-cyclopentyl | H | S | O | 1-cyano-cyclopropyl |
| H | F | OCH₂CO₂C₂H₅ | H | S | O | 1-methylcyclopropyl |

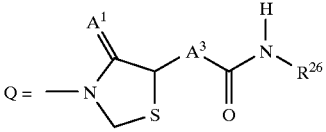

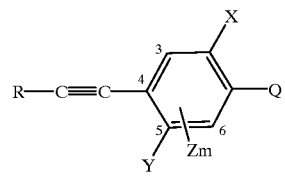

| R | X | Y | Zm | A¹ | A² | R²⁶ |
|---|---|---|----|----|----|-----|
| H | F | OCH(CH₃)₂ | H | O | CH₂ | 1,1-dimethyl-2-propynyl |
| H | F | NHSO₂C₂H₅ | H | S | CH₂ | 1,1-dimethyl-2-propynyl |
| H | F | O-cyclopentyl | H | O | CH₂ | C(CH₃)₃ |

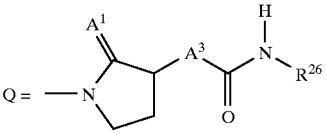

| R | X | Y | Zm | R⁵ |
|---|---|---|----|-----|
| Si(CH₃)₃ | F | OCH₃ | H | CH₃ |
| H | F | OCH₃ | H | CHF₂ |

TABLE 1-continued

| | | | | |
|---|---|---|---|---|
| H | F | OCH(CH$_3$)$_2$ | H | CHF$_2$ |
| H | F | O-cyclopentyl | H | CHF$_2$ |
| H | F | OCH(CH$_3$)$_2$ | H | CH$_2$CH$_2$CH$_2$F |
| H | F | NHSO$_2$CH$_3$ | H | CHF$_2$ |
| H | F | NHSO$_2$C$_2$H$_5$ | H | CHF$_2$ |
| H | F | NHSO$_2$C$_2$H$_5$ | H | CH$_2$CH$_2$CH$_2$F |
| H | F | OCH$_2$CO$_2$C$_2$H$_5$ | H | CHF$_2$ |
| H | F | S-cyclopentyl | H | CHF$_2$ |
| H | H | OCF$_3$ | H | CHF$_2$ |
| H | F | OCH(CH$_3$)$_2$ | H | cyclopropyl |
| H | F | O-cyclopentyl | H | C(CH$_3$)$_3$ |
| H | F | OCHF$_2$ | H | CHF$_2$ |

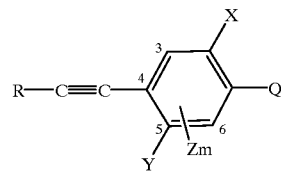

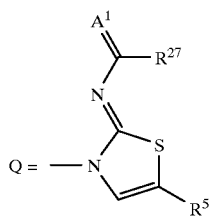

| R | X | Y | Zm | A$^1$ | R$^5$ | R$^{27}$ |
|---|---|---|---|---|---|---|
| Si(CH$_3$)$_3$ | F | OCH$_3$ | H | O | CH$_3$ | CH$_3$ |
| H | F | OCH(CH$_3$)$_2$ | H | O | C$_2$H$_5$ | CF$_3$ |
| H | F | O-cyclopentyl | H | O | C$_2$H$_5$ | CF$_3$ |
| H | F | OCH$_3$ | H | S | C$_2$H$_5$ | CF$_3$ |
| H | F | OCH(CH$_3$)$_2$ | H | S | C$_2$H$_5$ | cyclopropyl |
| H | F | O-cyclopentyl | H | S | CH$_3$ | CF$_3$ |
| H | F | NHSO$_2$CH$_3$ | H | O | C$_2$H$_5$ | CF$_3$ |
| H | F | NHSO$_2$CH$_3$ | H | S | C$_2$H$_5$ | CF$_3$ |
| H | F | OCH(CH$_3$)$_2$ | H | O | C$_2$H$_5$ | OCH$_2$CF$_3$ |
| H | F | OCH$_3$ | H | O | C$_2$H$_5$ | C(CH$_3$)$_3$ |

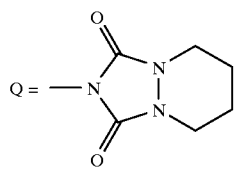

| R | X | Y | Zm |
|---|---|---|---|
| H | F | OC$_2$H$_5$ | H |

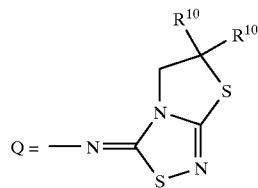

| R | X | Y | Zm | R$^{10}$ | R$^{10}$ |
|---|---|---|---|---|---|
| H | F | OCH(CH$_3$)$_2$ | H | CH$_3$ | CH$_3$ |

TABLE 1-continued

[Structure: R—C≡C— attached to benzene ring with positions labeled 3,4,5,6, substituents X (position 3), Q (position 6), Y (position 5), Zm (position 6 area)]

[Structure for Q: =N connected to bicyclic ring with R¹⁰, R¹⁰ substituents, containing N, S, N ring]

| R | X | Y | Zm | R¹⁰ | R¹⁰ |
|---|---|---|----|-----|-----|
| H | F | OCH₃ | H | CH₃ | CH₃ |

[Structure for Q: =N connected to bicyclic ring with R¹⁰, R²⁸ substituents, containing N, S, with =A¹]

| R | X | Y | Zm | A¹ | R¹⁰ | R²⁸ |
|---|---|---|----|----|-----|-----|
| H | F | O-cyclopropyl | H | O | H | H |
| H | F | OC₂H₅ | H | O | Cl | H |

[Structure for Q: =N connected to bicyclic ring with six-membered and five-membered rings fused, containing N, S, with =A¹]

| R | X | Y | Zm | A¹ |
|---|---|---|----|----|
| H | F | OCH(CH₃)₂ | H | O |

[Structure for Q: =N connected to bicyclic pyrrolizidine-type ring containing N, S, with =A¹]

| R | X | Y | Zm | A¹ |
|---|---|---|----|----|
| H | F | OCH₂CO₂C₂H₅ | H | O |
| H | F | OCH₃ | H | O |

When in the process (a), for example 3-(4-bromo-5-ethoxy-2-fluorophenyl)-1-methyl-6-trifluoro-methyl-2,4(1H,3H)-pyrimidinedione and trimethylsilylacetylene are used as the starting materials, the course of the reaction can be represented by the following equation:

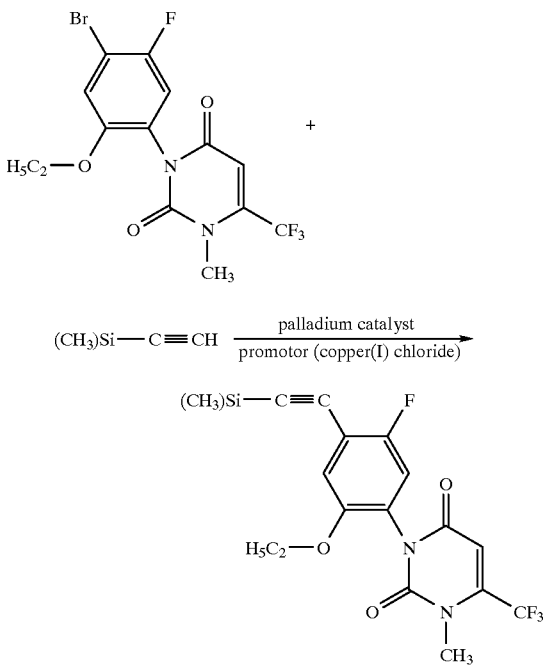

When in the process (b), for example 3-(5-ethoxy-2-fluoro-4-{2-(trimethylsilyl)-1-ethynyl}phenyl)-1-methyl-6-trifluoromethyl-2,4(1H, 3H)-pyrimidinedione is desilylated by potassium fluoride, the course of the raction can be represented by the following equation:

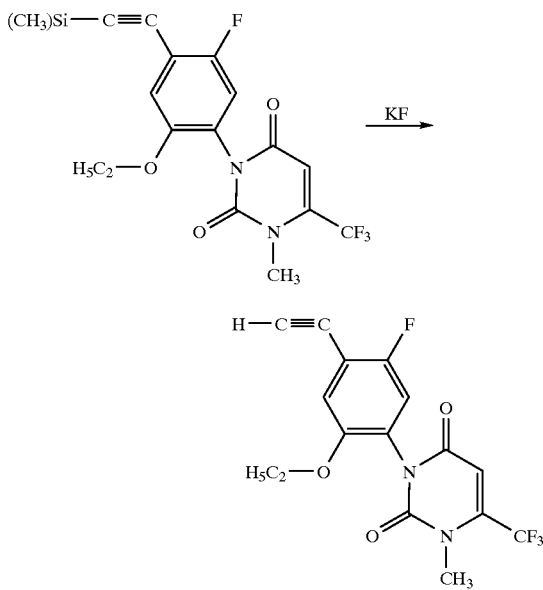

The first starting materials used in the process (a) according to the invention are those as definied by formula (II) above.

In the process (a) according to the invention, the starting materials of the formula (II) mean based on the above definitions of X, Y, Z, m, Q and hal, prefearbly substituents based on the above preferred definitions of X, Y, Z, m and Q.

The above process (a) can be conducted according to Tetrahedron Letters 1975, 4467. The compounds of the formula (II) used as the starting material are known compounds which are described in the above-mentioned prior art literatures, or they can be synthesized by the same processes as described in the above-mentioned prior art literatures.

Examples of the compounds of the formula (II) are as follows:

3-(4-bromophenyl)-1-methyl-6-trifluoromethyl-2,4 (1H, 3H)-pyrimidinedione, 3-(4-iodophenyl)-1-methyl-6-trifluoromethyl-2,4 (1H, 3H)-pyrimidinedione, 3-(4-bromo-2-fluorophenyl)-1-methyl-6-trifluoromethyl-2,4 (1H, 3H)-pyrimidinedione, 3-(4-bromo-2-fluoro-5-methoxyphenyl)-1-methyl-6-trifluoromethyl-2,4(1H, 3H)-pyrimidinedione, 3-(4-bromo-5-ethoxy-2-fluorophenyl)-1-methyl-6-trifluoromethyl-2,4(1H, 3H)pyrimidinedione, 3-(4-bromo-2-fluoro-5-propoxyphenyl)-1-methyl-6-trifluoromethyl-2,4(1H,3H)-pyrimidinedione, 3-(4-bromo-2-fluoro-5-isopropoxyphenyl)-1-methyl-6-trifluoromethyl-2,4(1H,3H)-pyrimidinedione, 3-(4-bromo-5-cyclopropoxy-2-fluorophenyl)-1-methyl-6-trifluoromethyl-2,4(1H, 3H)-pyrimidinedione, 3-(4-bromo-5-cyclopentyloxy-2-fluorophenyl)-1-methyl-6-trifluoromethyl-2,4(1H, 3H)-pyrimidinedione, 3-(4-bromo-2-fluoro-5-methoxymethoxyphenyl)-1-methyl-6-trifluoromethyl-2,4(1H, 3H)-pyrimidinedione, 3-(4-bromo-2-fluoro-5-methoxycarbonylmethoxyphenyl)-1-methyl-6-trifluoromethyl-2,4(1H,3H)-pyrimidinedione, 3-(4-bromo-5-ethoxycarbonylmethoxy-2-fluorophenyl)-1-methyl-6-trifluoromethyl-2,4 (1H,3H)-pyrimidinedione, 3-(4-bromo-5-isopropoxy-2-fluorophenyl)-1,5-dimethyl-6-trifluoromethyl-2,4(1H,3H)-pyrimidinedione, 3-(4-bromo-2-fluoro-5-methylthiophenyl)-1-methyl-6-trifluoromethyl-2,4(1H,3H)-pyrimidinedione, 3-(4-bromo-5-ethylthio-2-fluorophenyl)-1-methyl-6-trifluoromethyl-2,4(1H,3H)-pyrimidinedione, 3-(4-bromo-2-fluoro-5-propylthiophenyl)-1-methyl-6-trifluoromethyl-2,4(1H,3H)-pyrimidinedione, 3-(4-bromo-2-fluoro-5-isopropylthiophenyl)-1-methyl-6-trifluoromethyl-2,4(1H,3H)-pyrimidinedione, 3-(4-bromo-5-cyclopropylthio-2-fluorophenyl)-1-methyl-6-trifluoromethyl-2,4(1H,3H)-pyrimidinedione, 3-(4-bromo-5-cyclopentylthio-2-fluorophenyl)-1-methyl-6-trifluoromethyl-2,4(1H,3H)-pyrimidinedione, 3-(4-bromo-2-fluoro-5-methoxymethylthiophenyl)-1-methyl-6-trifluoromethyl-2,4(1H,3H)-pyrimidinedione, 3-(4-bromo-2-fluoro-5-methoxycarbonylmethylthiophenyl)-1-methyl-6-trifluoromethyl-2,4(1H,3H)-pyrimidinedione, 3-(4-bromo-5-ethoxycarbonylmethylthio-2-fluorophenyl)-1-methyl-6-trifluoromethyl-2,4(1H,3H)-pyrimidinedione, 3-(4-bromo-2-fluoro-5-methylsulfonylphenyl)-1-methyl-6-trifluoromethyl-2,4(1H,3H)-pyrimidinedione, 3-(4-bromo-5-ethylsulfonyl-2-fluorophenyl)-1-methyl-6-trifluoromethyl-2,4(1H,3H)-pyrimidinedione, 3-(4-bromo-5-cyclopentylsulfonyl-2-fluorophenyl)-1-methyl-6-trifluoromethyl-2,4(1H,3H)-pyrimidinedione, 3-(4-bromo-2-fluoro-5-methylsulfinylphenyl)-1-methyl-6-trifluoromethyl-2,4(1H,3H)-pyrimidinedione, 3-(4-bromo-5-ethylsulfinyl-2-fluorophenyl)-1-methyl-6-trifluoromethyl-2,4(1H,3H)-pyrimidinedione, 3-(4-bromo-5-cyclopentylsulfinyl-2-fluorophenyl)-1-methyl-6-trifluoromethyl-2,4(1H,3H)-pyrimidinedione, 3-(4-bromo-2-fluoro-5-nitrophenyl)-1-methyl-6-trifluoromethyl-2,4(1H,3H)-pyrimidinedione, 3-(4-bromo-2-fluoro-5-nitrophenyl)-1,5-dimethyl-6-trifluoromethyl-2,4(1H,3H)-pyrimidinedione, methyl 2-bromo-5-[3,6-dihydro-2,6-dioxo-3-methyl-4-trifluoromethyl-1(2H)-pyrimidinyl]-4-fluorobenzoate, ethyl 2-bromo-5-[3,6-dihydro-2,6-dioxo-3-methyl-4-trifluoromethyl-1(2H)-pyimidinyl]-4-fluorobenzoate, isopropyl 2-bromo-5-[3,6-dihydro-2,6-dioxo-3-methyl-4-trifluoromethyl-1(2H)-pyrimidinyl]-4-fluoro-benzoate, isopropyl 2-bromo-5-[3,6-dihydro-2,6-dioxo-3,5-dimethyl-4-trifluoromethyl-1(2H)pyrimidinyl]-4-fluorobenzoate, 3-(7-bromo-5-fluoro-2-methyl-2,3-dihydrobenzo[b]furan-4-yl)-1-methyl-6-trifluoromethyl-2,4(1H,3H)-pyrimidinedione, 3-(7-bromo-5-fluoro-2-hydroxymethyl-2,3-dihydrobenzo[b]furan-4-yl)-1-methyl-6-trifluoromethyl-2,4(1H,3H)-pyrimidinedione, 3-(7-bromo-5-fluoro-2-methoxymethyl-2,3-dihydrobenzo[b]furan-4-yl)-1-methyl-6-trifluoromethyl-2,4(1H,3H)-pyrimidinedione, methyl 7-bromo-4-[3,6-dihydro-2,6-dioxo-3,5-dimethyl-4-trifluoromethyl-1(2H)-pyrimidinyl]-5-fluoro-2,3-dihydrobenzo[b]furan-2-carboxylate, 3-(7-bromo-5-fluoro-2,2-dimethyl-2,3-dihydro-benzo[b]furan-4-yl)-1-methyl-6-trifluoromethyl-2,4(1H,3H)-pyrimidinedione,.

3-(7-bromo-5-fluoro-2-hydroxymethyl-2-ethyl-2,3-dihydrobenzo[b]furan-4-yl)-1-methyl-6-trifluoromethyl-2,4(1H, 3H)-pyrimidinedione, 3-(7-bromo-5-fluoro-2-methoxymethyl-2-methyl-2,3-dihydrobenzo[b]furan-4-yl)-1-methyl-6-trifluoromethyl-2,4(1H, 3H)-pyrimidinedione, methyl 7-bromo-5-fluoro-2-methyl-4-[3,6-dihydro-2,6-dioxo-3,5-dimethyl-4-trifluoromethyl-1(2H)-pyrimidinyl]-2,3-dihydrobenzo[b]furan-2-carboxylate, 3-(7-bromo-5-fluoro-2-methylbenzo[b]furan-4-yl)-1-methyl-6-trifluoromethyl-2,4(1H,3H)-pyrimidinedione, 1-(4-bromo-2-fluoro-5-methoxyphenyl)-4-(3-fluoropropyl)-4,5-dihydro-1H-1,2,3,4-tetrazol-5-one, 1-(4-bromo-2-fluoro-5-nitrophenyl)-4-(3-fluoropropyl)-4,5-dihydro-1H-1,2,3,4-tetrazol-5-one, 1-(4-bromo-2-fluoro-5-methoxyphenyl)-4-difluoromethyl-4,5-dihydro-1H-1,2,3,4-tetrazol-5-one, 1-(4-bromo-2-fluoro-5-nitrophenyl)-4-difluoromethyl-4,5-dihydro-1H-1,2,3,4-tetrazol-5-one, 3-(4-bromo-2-fluorophenyl)-4-chloro-5-difluoromethoxy-1-methyl-1H-pyrazole, 3-(4-bromo-2-fluoro-5-methoxyphenyl)-4-chloro-5-difluoromethoxy-1-methyl-1H-pyrazole, 3-(4-bromo-2-fluoro-5-nitrophenyl)-4-chloro-5-difluoromethoxy-1-methyl-1H-pyrazole, 1-(4-bromo-2-fluoro-5-methoxyphenyl)-4-difluoromethyl-3-methyl-4,5-dihydro-1H-1,2,4-triazol-5-one, 1-(4-bromo-2-fluoro-5-nitrophenyl)-4-difluoromethyl-3-methyl-4,5-dihydro-1H-1,2,4-triazol-5-one, 2-(4-bromo-2-fluoro-5-methoxyphenyl)-4-methyl-2,3,4,5-tetrahydro-1,2,4-triazin-3,5-dione, N-(4-bromo-2-fluoro-5-methoxyphenyl)-3,4,5,6-tetrahydrophthalimide, N-(4-bromo-2-fluoro-5-isopropoxyphenyl)-3,4,5,6-tetrahydrophthalimide, N-(4-bromo-2-fluoro-5-nitrophenyl)-3,4,5,6-tetrahydrophthalimide, 2-(4-bromo-2-fluoro-5-methoxyphenyl)perhydro-[1,2,4]triazolo[1,2-a]pyridazin-1,3-dione, 3-(4-bromo-2-fluoro-5-isopropoxyphenylimino)-5,6-dihydro-6,6-dimethyl-3H-thiazolo[2,3-C][1,2,4]thiaziazole, 3-(4-bromo-2-fluoro-5-methoxyphenylimino)-6,7-dihydro-6,6-dimethyl-3H,5H-pyrrolo[2,1-C][1,2,4]thiaziazole, and the like.

The second starting materials used in the process (a) according to the invention are those as defined by formula (III) above.

The compounds of the formula (III) used as the starting material of the process (a) are well known in the field of organic chemistry and examples thereof include trimethylsilylacetylene, 3,3-dimethyl-1-butyne, propyne, 1-hexyne, ethynylbenzene, and the like.

The starting materials used in the process (b) according to the invention are those as defined by formula (Ia) above.

In the process (b), the compounds of the formula (Ia) used as the starting material are those which can be synthesized by the above process (a), and constitute a part of the compounds of the invention.

Examples of the compounds of the formula (Ia) are as follows:

3-{4-[2-(trimethylsilyl)-1-ethynyl]phenyl}-1-methyl-6-trifluoromethyl-2,4(1,3H)-pyrimidinedione, 3-{2-fluoro-4-[2-(trimethylsilyl)-1-ethynyl]phenyl}-1-methyl-6-trifluoromethyl-2,4(1H,3H)-pyrimidinedione, 3-{2-fluoro-5-methoxy-4-[2-(trimethylsilyl)-1-ethynyl]phenyl}-1-methyl-6-trifluoromethyl-2,4(1,3H)-pyrimidinedione, 3-{5-ethoxy-2-fluoro-4-[2-(trimethylsilyl)-1-ethynyl]phenyl}-1-methyl-6-trifluoromethyl-2,4(1H,3H)-pyrimidinedione, 3-{2-fluoro-5-propoxy-4-[2-(trimethylsilyl)-1-ethynyl]phenyl}-1-methyl-6-trifluoromethyl-2,4(1H,3H)-pyrimidinedione, 3-{2-fluoro-5-isopropoxy-4-[2-(trimethylsilyl)-1-ethynyl]phenyl}-1-methyl-6trifluoromethyl-2,4(1H,3H)-pyrimidinedione, 3-{5-cyclopropoxy-2-fluoro-4-[2-(trimethylsilyl)-1-ethynyl]phenyl}-1-methyl-6-trifluoromethyl-2,4(1H,3H)-pyrimidinedione, 3-{5-cyclopentyloxy-2-fluoro-4-[2-(trimethylsilyl)-1-ethynyl]phenyl}-1-methyl-6-trifluoromethyl-2,4(1H,3H)-pyrimidinedione, 3-{2-fluoro-5-methoxymethoxy-4-[2-(trimethylsilyl)-1-ethynyl]phenyl}-1-methyl-6-trifluoromethyl-2,4(1H,3H)-pyrimidinedione, 3-{2-fluoro-5-methoxycarbonylmethoxy-4-[2-(trimethylsilyl)-1-ethynyl]phenyl}-1-methyl-6-trifluoromethyl-2,4(1H,3H)-pyrimidinedione, 3-{5-ethoxycarbonylmethoxy-2-fluoro-4-[2-(trimethylsilyl)-1-ethynyl]phenyl}-1-methyl-6-trifluoromethyl-2,4(1H,3H)-pyrimidinedione, 3-{2-fluoro-5-isopropoxy-4-[2-(trimethylsilyl)-1-ethynyl]phenyl}-1,5-dimethyl-6trifluoromethyl-2,4(1H,3H)-pyrimidinedione, 3-{2-fluoro-5-methylthio-4-[2-(trimethylsilyl)-1-ethynyl]phenyl}-1-methyl-6-trifluoromethyl-2,4(1H,3H)-pyrimidinedione, 3-{5-ethylthio-2-fluoro-4-[2-(trimethylsilyl)-1-ethynyl]phenyl}-1-methyl-6-trifluoromethyl-2,4(1H,3H)-pyrimidinedione, 3-{2-fluoro-5-propylthio-4-[2-(trimethylsilyl)-1-ethynyl]phenyl}-1-methyl-6-trifluoromethyl-2,4(1H,3H)-pyrimidinedione, 3-{2-fluoro-5-isopropylthio-4-[2-(trimethylsilyl)-1-ethynyl]phenyl}-1-methyl-6-trifluoromethyl-2,4(1H,3H)-pyrimidinedione, 3-{5-cyclopropylthio-2-fluoro-4-[2-(trimethylsilyl)-1-ethynyl]phenyl}-1-methyl-6-trifluoromethyl-2,4(1H,3H)-pyrimidinedione, 3-{5-cyclopentylthio-2-fluoro-4-[2-(trimethylsilyl)-1-ethynyl]phenyl}-1-methyl-6-trifluoromethyl-2,4(1H,3H)-pyrimidinedione, 3-{2-fluoro-5-methoxymethylthio-4-[2-(trimethylsilyl)-1-ethyhyl]phenyl}-1-methyl-6-trifluoromethyl-2,4(1H,3H)-pyrimidinedione, 3-{2-fluoro-5-methoxycarbonylmethylthio-4-[2-(trimethylsilyl)-1-ethynyl]phenyl}-1-methyl-6-trifluoromethyl-2,4(1H,3H)-pyrimidinedione, 3-{5-ethoxycarbonylmethylthio-2-fluoro-4-[2-(trimethylsilyl)-1-ethynyl]phenyl}-1-methyl-6-trifluoromethyl-2,4(1H,-3H)-pyrimidinedione, 3-{2-fluoro-5-methylsulfonyl-4-[2-(trimethylsilyl)-1-ethynyl]phenyl}-1-methyl-6-trifluoromethyl-2,4(1H,3H)-pyrimidinedione,.

3-{5-ethylsulfonyl-2-fluoro-4-[2-(trimethylsilyl)-1-ethynyl]phenyl}-1-methyl-6-trifluoromethyl-2,4(1H,3H)-pyrimidinedione, 3-{5-cyclopentylsulfonyl-2-fluoro-4-[2-(trimethylsilyl)-1-ethynyl]phenyl}-1-methyl-6-trifluoromethyl-2,4(1H,3H)-pyrimidinedione, 3-{2-fluoro-5-methylsulfinyl-4-[2-(trimethylsilyl)-1-ethynyl]phenyl}-1-methyl-6-trifluoromethyl-2,4(1H,3H)-pyrimidinedione, 3-{5-ethylsulfinyl-2-fluoro-4-[2-(trimethylsilyl)-1-ethynyl]phenyl}-1-methyl-6-trifluoromethyl-2,4(1H,3H)-pyrimidinedione, 3-{5-cyclopentylsulfinyl-2-fluoro-4-[2-(trimethylsilyl)-1-ethynyl]phenyl}-1-methyl-6-trifluoromethyl-2,4(1H,3H)-pyrimidinedione, 3-{5-amino-2-fluoro-4-[2-(trimethylsilyl)-1-ethynyl]phenyl}-1-methyl-6-trifluoromethyl-2,4(1H,3H)-pyrimidinedione, 3-{5-amino-2-fluoro-4-[2-(trimethylsilyl)-1-ethynyl]phenyl}-1,5-dimethyl-6-trifluoromethyl-2,4(1H,3H)-pyrimidinedione, methyl 5-[3,6-dihydro-2,6-dioxo-3-methyl-4-trifluoromethyl-1(2H)-pyrimidinyl]-4-fluoro-2-[2-(trimethylsilyl)1-ethynyl]benzoate, ethyl 5-[3,6-dihydro-2,6-dioxo-3-methyl-4-trifluoromethyl-1(2H)-pyrimidinyl]-4-fluoro-2-[2-(trimethylsilyl)-1-ethynyl]benzoate, isopropyl 5-[3,6-dihydro-2,6-dioxo-3-methyl-4-trifluoromethyl-1(2H)-pyrimidinyl]-4-fluoro-2-[2-(trimethylsilyl)-1-ethynyl]benzoate, isopropyl 5-[3,6-dihydro-2,6-dioxo-3,5-dimethyl-4-trifluoromethyl-1(2H)-pyrimidinyl]-4-fluoro-2-[2-(trimethylsilyl)-1-ethynyl]benzoate, 3-{5-fluoro-2-methyl-7-[2-(trimethylsilyl)-1-ethynyl]-2,3-dihydrobenzo[b]furan-4-yl}-1-methyl-6-trifluoromethyl-2,4(1H,3H)-pyrimidinedione, 3-{5-fluoro-2-hydroxymethyl-7-[2-(trimethylsilyl)-1-ethynyl]-2,3-dihydrobenzo[b]furan-4-yl}-1-methyl-6-trifluoromethyl-2,4(1H,3H)-pyrimidinedione, 3-{5-fluoro-2-methoxymethyl-7-[2-(trimethylsilyl)-1-ethynyl]-2,3-dihydrobenzo[b]furan-4-yl}-1-methyl-6-trifluoromethyl-2,4(1,3H)-pyrimidinedione, methyl 4-[3,6-dihydro-2,6-dioxo-3,5-dimethyl-4-trifluoromethyl-1(2H)-pyrimidinyl]-5-fluoro-7-[2-(trimethylsilyl)-1-ethynyl]-2,3-dihydrobenzo[b]furan-2-carboxylate, 3-{5-fluoro-2,2-dimethyl-7-[2-(trimethylsilyl)-1-ethynyl]-2,3-dihydrobenzo[b]furan-4-yl}-1-methyl-6-trifluoromethyl-2,4(1H,3H)-pyrimidinedione, 3-{5-fluoro-2-hydroxymethyl-2-methyl-7-[2-(trimethylsilyl)-1-ethynyl]-2,3-dihydrobenzo[b]furan-4-yl}-1-methyl-6-trifluoromethyl-2,4(1H,3H)-pyrimidinedione, 3-{5-fluoro-2-methoxymethyl-2-methyl-7-[2-(trimethylsilyl)-1-ethynyl]-2,3-dihydrobenzo[b]furan-4-yl}-1-methyl-6-trifluoromethyl-2,4(1H,3H)-pyrimidinedione, methyl 4-[3,6-dihydro-2,6-dioxo-3,5-dimethyl-4-trifluoromethyl-1(2H)-pyrimidinyl]-5-fluoro-2-methyl-7-[2-(trimethylsilyl)-1-ethynyl]-2,3-dihydrobenzo[b]furan-2-carboxylate, 3-{5-fluoro-2-methyl-7-[2-(trimethylsilyl)-1-ethynyl]-benzo[b]furan-4-yl}-1-methyl-6-trifluoro-methyl-2,4(1H,3H)-pyrimidinedione, 1-{2-fluoro-5-methoxy-4-[2-(trimethylsilyl)-1-ethynyl]phenyl}-4-(3-fluoropropyl)-4,5-dihydro-1H-1,2,3,4-tetrazol-5-one, 1-{2-fluoro-5-nitro-4-[2-(trimethylsilyl)-1-ethynyl]phenyl}-4-(3-fluoropropyl)-4,5-dihydro-1H-1,2,3,4-tetrazol-5-one, 1-difluoromethyl-4-{2-fluoro-5-methoxy-4-[2-(trimethylsilyl)-1-ethynyl]phenyl}-4,5dihydro-1H-1,2,3,4-tetrazol-5-one, 1-difluoromethyl-4-{2-fluoro-5-nitro-4-[2-(trimethylsilyl)-1-ethynyl]phenyl}-4,5dihydro-1H-1,2,3,4-tetrazol-5-one, 4-chloro-5-difluoromethoxy-3-{2-fluoro-4-[2-(trimethylsilyl)-1-ethynyl]phenyl}-1-methyl-1H-pyrazole, 4-chloro-5-difluoromethoxy-3-{2-fluoro-5-methoxy-4-[2-(trimethylsilyl)-1-ethynyl]phenyl}-1-methyl-1H-pyrazole, 4-chloro-5-difluoromethoxy-3-{2-fluoro-5-nitro-4-[2-(trimethylsilyl)-1-ethynyl]phenyl}-1-methyl-1H-pyrazole, 4-difluoromethyl-1-{2-fluoro-5-methoxy-4-[2-(trimethylsilyl)-1-ethynyl]phenyl}-3-methyl-4,5-dihydro-1H-1,2,4-triazol-5-one, 4-difluoromethyl-1-{2-fluoro-5-nitro-4-[2-(trimethylsilyl)-1-ethynyl]phenyl}-3-methyl-4,5-dihydro-1H-1,2,4-triazol-5-one, 2-{2-fluoro-5-methoxy-4-[2-(trimethylsilyl)-1-ethynyl]phenyl}-4-methyl-2,3,4,5-tetrahydro-1,2,4-triazine-3,5-dione, N-{2-fluoro-5-methoxy-4-[2-(trimethylsilyl)-1-ethynyl] phenyl}-3,4,5,6-tetrahydrophthalimide, N-{2-fluoro-5-isopropoxy-4-[2-(trimethylsilyl)-1-ethynyl]phenyl}-3,4,5,6-tetrahydrophthalimide, N-{2-fluoro-5-nitro-4-[2-(trimethylsilyl)-1-ethynyl] phenyl}-3,4,5,6-tetrahydrophthalimide, 2-{2-fluoro-5-methoxy-4-[2-(trimethylsilyl)-1-ethynyl] phenyl}perhydro[1,2,4]triazolo[1,2-a]pyridazine-1,3-dione, 3-{2-fluoro-5-methoxy-4-[2-(trimethylsilyl)-1-ethynyl] phenyl}-5,6-dihydro-6,6-dimethyl-3H-thiazolo[2,3-C][1,2,4]thiadiazole, 3-(2-fluoro-5-methoxy-4-[2-(trimethylsilyl)-1-ethynyl] phenyl}-6,7-dihydro-6,6-dimethyl-3H,5H-pyrrolo[2,1-C][1,2,4]thiadiazole, and the like.

Examples of desilylating agents used in the above process (b) include potassium fluoride, tetrabutylammonium fluoride, sodium hydrogencarbonate, potassium hydrogencarbonate, sodium carbonate, potassium carbonate, sodium hydroxide, potassium hydroxide, lithium hydroxide, calcium hydroxide, and the like.

The reaction of the above process (a) can be carried out in the presence of inert solvents. Examples of usable solvents are: aliphatic, alicyclic or aromatic hydrocarbons (which may optionally be chlorinated) such as pentane, hexane, cyclohexane, petroleum ether, ligroin, benzene, toluene and xylene; ethers such as ethyl ether, methyl ethyl ether, isopropyl ether, butyl ether, dioxane, dimethoxyethane (DME), tetrahydrofuran (TTh) and diethylene glycol dimethyl ether (DGM); nitriles such as acetonitrile, propionitrile and acrylonitrile; acid amides such as dimethylformamide (DMF), dimethylacetamide (DMA), N-methylpyrrolidone, 1,3-dimethyl-2-imidazolidinone and hexamethylphosphoric triamide (HMPA); and bases such as pyridine, diethylamine, diisopropylamine, piperidine, pyrrolidine, triethylamine and tributylanine.

The reaction of the process (a) can be carried out in the presence of an acid binder. Examples of usable acid binding agents, which may be mentioned, are: inorganic bases, for example, carbonates and bicarbonates of alkali metals or alkaline earth metals, such as sodium hydrogencarbonate, potassium hydrogencarbonate, sodium carbonate and potassium carbonate; organic bases, for example, tertiary amines, dialkylaminoanilines and pyridines, such as triethylamine, tributylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU); organic lithium compounds, such as methyl lithium, n-butyl lithium, sec-butyl lithium, tert-butyl lithium, phenyllithium, dimethyl copper lithium, lithium diisopropylamide, lithium cyclohexylisopropylamide, lithium dicyclohexylamide, n-butyl lithium-DABCO, n-butyl lithium-DBU and n-butyl lithium-TMEDA.

The reaction of the process (a) is preferably conducted in the presence of a palladium catalyst and a promotor. Examples of the palladium catalysts include dichlorobis (triphenylphosphine)palladium, tetrakistriphenylphosphine palladium, palladium chloride-triphenylphosphine, palladium acetate-triphenylphosphine, and the like. Further, examples of the promoters include, for example, copper(I) iodide.

The reaction of the process (a) can be conducted at a temperature within a substantially broad range, but it is preferred to carry out a reaction at a temperature of about −80 to about 150° C., preferably about 0 to about 120° C. Further, the reaction should preferably be conducted under normal pressure but it may optionally be operated under elevated or reduced pressure.

For carrying out the process (a), for instance, 1 mole of the compound of the formula (II) can be reacted with 1 to 5 molar amounts of the compound of the formula (III) in a solvent such as tetrahydrofuran in the presence of a palladium catalyst (0.005 to 0.2 molar amount), copper(I) chloride (0.005 to 0.2 molar amount) and an acid binding agent (1 to 5 molar amounts) to thereby obtain the objective compound of the formula (I).

The reaction of the above process (b) can also be carried out in the presence of appropriate inert solvents. Examples of usable solvents are: water; aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichloro-benzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methylisopropyl ketone and methyl isobutylketone (MIBK); nitrites such as acetonitrile, propionitrile and acrylonitrile; alcohols such as methanol, ethanol, isopropanol, butanol and ethylene glycol; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulforan; and bases such as pyridine.

The reaction of the process (b) can be conducted at a temperature within a substantially broad range, but it is preferred to carry out a reaction at a temperature of about −80 to about 150° C., preferably about −20 to about 120° C. Further, the reaction should preferably be conducted under normal pressure but it may optionally be operated under elevated or reduced pressure.

For carrying out the process (b), for instance, 1 mole of the compound of the formula (Ia) can be reacted with 1 to 3 molar amounts of a desilylating agent in a diluent such as ethanol to thereby obtain the objective compound of formula (I).

The compounds of formula (I) according to the invention can also be synthesized by processes which are different from the above processes (a) and (b).

Specific explanations are given hereafter considering for example a case of producing the compounds of the formula (I) wherein Q is a heterocyclic group represented by the formula:

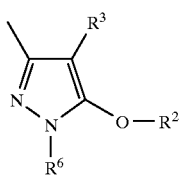

The respective compounds of formula (I) can be synthesized by the following process:

(c) in the case where $R^3$ is chlorine:

compounds of the formula (IV)

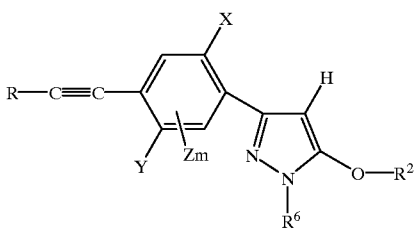

wherein R, $R^2$, $R^6$, X, Y, Z and m are defined as above, are reacted with chlorine gas or sulfuryl chloride, if appropriate, in the presence of inert solvents, or (d) in the case where $R^2$ is $C_{1-6}$ haloallyl and $R^3$ is hydrogen:

compounds of the formula (V)

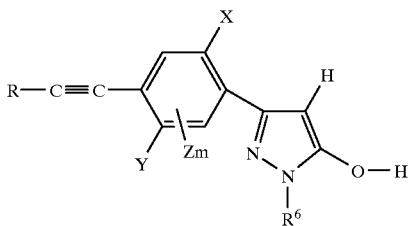

wherein R, $R^6$, X Y, Z and m are defined as above, are reacted with halides of the formula (VI)

wherein hal and $R^2$ are defined as above, in the presence of inert solvents and, if approproate, in the presence of an acid binder, or (e) in the case where $R^2$ and $R^3$ represent hydrogen:
compounds of the formula (VII)

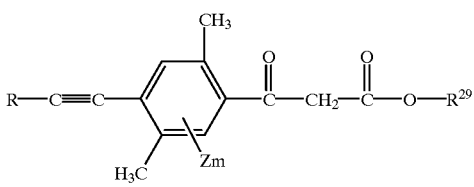

wherein R, X, Y, Z and m are defined as above, and $R^{29}$ is methyl or ethyl, are reacted with compounds of the formula (VIII)

wherein $R^6$ is defined as above, in the presence of inert solvents.

In the above process (c), the compounds of formula (IV) used as the starting material are included in the compounds of formula (I) according to the invention, and can be synthesized, for example, by the above process (d). The chlorination of the compounds of formula (IV) by use of chlorine gas or sulfonyl chloride can be carried out by the methods which are well known in the field of organic chemistry.

In the above process (d), the compounds of formula (V) used as the starting material are included in the compounds of formula (I) according to the invention, and can be synthesized, for example, by the above process (e).

In the process (d), the compounds of formula (VI) used as the starting material are well known in the field of organic chemistry.

The reaction of the compounds of formula (V) with the halide of formula (VI) according to the process (d) can be carried out by the methods which are well known in the field of organic chemistry.

In the above process (e), the compounds of the formula (VII) used as the starting material are as follows:

methyl 3-{2-fluoro-4-[2-(trimethylsilyl)-1-ethynyl]phenyl}-3-oxopropionate, ethyl 3-{2-fluoro-4-[2-(trimethylsilyl)-1-ethynyl]phenyl}-3-oxopropionate, methyl 3-[-4-(1-ethynyl)-2-fluorophenyl]-3-oxopropionate, ethyl 3-[-4-(1-ethynyl)-2-fluorophenyl]-3-oxopropionate, methyl 3-{5-cyanomethoxy-2-fluoro-4-[2-(trimethylsilyl)-1-ethynyl]phenyl}-3-oxopropionate, ethyl 3-{5-cyanomethoxy-2-fluoro-4-[2-(trimethylsilyl)-1-ethynyl]phenyl}-3-oxopropionate, methyl 3-[5-cyanomethoxy-4-(1-ethynyl)-2-fluorophenyl}-3-oxopropionate, ethyl 3-[5-cyanomethoxy-4-(1-ethynyl)-2-fluorophenyl}-3-oxopropionate, methyl 3-{5-aminocarbonylmethoxy-2-fluoro-4-[2-(trimethylsilyl)-1-ethynyl]phenyl}-3-oxopropionate, ethyl 3-{5-aminocarbonylmethoxy-2-fluoro-4-[2-(trimethylsilyl)-1-ethynyl]phenyl}-3-oxopropionate, methyl 3-[5-aminocarbonylmethoxy-4-(1-ethynyl)-2-fluorophenyl]-3-oxopropionate, ethyl 3-[5-aminocarbonylmethoxy-4-(1-ethynyl)-2-fluorophenyl]-3-oxopropionate, methyl 3-{2-fluoro-5-methoxy-4-[2-trimethylsilyl)-1-ethynyl]phenyl}-3-oxopropionate, ethyl 3-{2-fluoro-5-methoxy-4-[2-trimethylsilyl)-1-ethynyl]phenyl}-3-oxopropionate, methyl 3-[4-(1-ethynyl)-2-fluoro-5-methoxyphenyl]-3-oxopropionate, ethyl 3-[4-(1-ethynyl)-2-fluoro-5-methoxyphenyl]-3-oxopropionate, and the like.

In the above process (e), the compounds of formula (VII) used as a starting material can be obtained, for instance, by the following processes:

(f) in the case where R is another group than hydrogen:
compounds of the formula (IX)

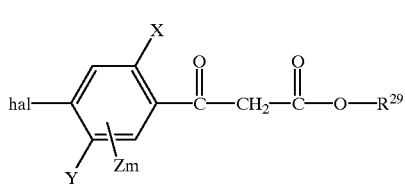

wherein $R^{29}$, hal, X, Y, Z and m are defined as above, are reacted with the compound of the above formula (III), in the presence of inert solvents, an acid binder, a catalyst and a promotor, or (g) in the case where R is hydrogen:

compounds of the formula (X)

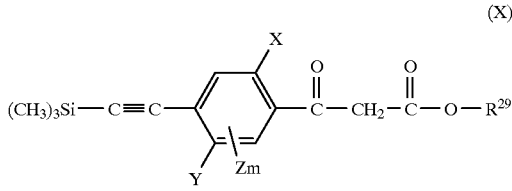
(X)

wherein $R^{29}$, X, Y, Z and m are defined as above are desilylated in the presence of inert solvents.

The reaction of the above process (f) can be conducted under the same conditions as those of the process (a) mentioned above. Examples of the compounds of the formula (IX) as the starting material are:

methyl 3-(4-bromo-2-fluorophenyl)-3-oxopropionate, ethyl 3-(4-bromo-2-fluorophenyl)-3-oxopropionate, methyl 3-(4-bromo-5-cyanomethoxy-2-fluorophenyl)-3-oxopropionate, ethyl 3-(4-bromo-5-cyanomethoxy-2-fluorophenyl)-3-oxopropionate, methyl 3-(5-aminocarbonylmethoxy-4-bromo-2-fluorophenyl)-3-oxopropionate, ethyl 3-(5-aminocarbonylmethoxy-4-bromo-2-fluorophenyl)-3-oxopropionate, methyl 3-(4-bromo-2-fluoro-5-methoxyphenyl)-3-oxopropionate, ethyl 3-(4-bromo-2-fluoro-5-methoxyphenyl)-3-oxopropionate, and the like.

The compounds of the formula (IX) can be synthesized, for instance, by the following processes:

(h) compounds of the formula (XI)

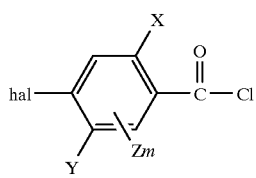
(XI)

wherein hal, X, Y, Z and m are defined as above, are reacted with compound of the formula:

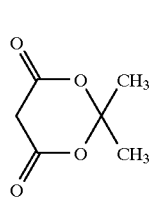
(XII)

in the presence of inert solvents and acid binder, or (i) compounds of the formula (XIII)

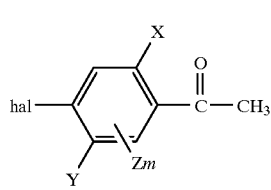
(XIII)

wherein hal, X, Y, Z and m are defined as above, are reacted with compounds of the formula (XIV)

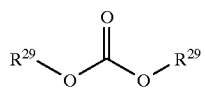
(XIV)

wherein $R^{29}$ is defined as above, in the presence of inert solvents and if appropriate in the presence of an acid binder.

Both processes (h) and (i) are well known in the field of organic chemistry, and the compounds of formulae (XI) to (XIV) used as the starting materials are known in the field of organic chemistry.

Examples of the compounds of formula (XI) include 4-bromo-2-fluorobenzoyl chloride, 4-bromo-5-cyanomethoxy-2-fluorobenzoyl chloride, 5-aminocarbonylmethoxy-4-bromo-2-fluorobenzoyl chloride, 4-bromo-2-fluoro-5-methoxybenzoyl chloride, and the like.

Examples of the compounds of formula (XIII) include 1-(4-bromo-2-fluorophenyl)-1-ethanone, 1-(4-bromo-5-cyanomethoxy-2-fluorophenyl)-1-ethanone, 1-(5-aminocarbsonylmethoxy-4-bromo-2-fluorophenyl)-1-ethanone, 1-(4-bromo-2-fluoro-5methoxyphenyl)-1-ethanone, and the like.

The reaction of the above process (g) can be conducted under the same conditions as those of the process (b) mentioned above. Examples of compounds of formula (X) used as the starting material include, methyl 3-{2-fluoro-4-[2-(trimethylsilyl)-1-ethynyl]phenyl}-3-oxopropionate, ethyl 3-{2-fluoro-4-[2-(trimethylsilyl)-1-ethynyl]phenyl}-3-oxopropionate, methyl 3-{5-cyanomethoxy-2-fluoro-4-[2-(trimethylsilyl)-1-ethynyl]phenyl}-3-oxopropionate, ethyl 3-{5-cyanomethoxy-2-fluoro-4-[2-(trimethylsilyl)-1-ethynyl]phenyl}-3-oxopropionate, methyl 3-{5-aninocarbonylmethoxy-2-fluoro-4-[2-(trimethylsilyl)-1-ethynyl]phenyl}-3-oxopropionate, ethyl 3-{5-aminocarbonylmethoxy-2-fluoro-4-[2-(trimethylsilyl)-1-ethynyl]phenyl}-3-oxopropionate, methyl 3-{2-fluoro-5-methoxy -4-[2-(trimethylsilyl)-1-ethynyl]phenyl}-3-oxopropionate, ethyl 3-{2-fluoro-5-methoxy-4-[2-(trimethylsilyl)-1-ethynyl]phenyl}-3-oxopropionate, and the like.

In the above process (g), the compounds of formula (X) used as the starting material can be produced by the above process (f).

The active compounds according to the invention can be used as defoliants, desiccants, agents for destroying broadleaved plants and, especially, as weedkillers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chloro-benzene, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or lattices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dye stuffs, azo dye stuffs or metal phthalocyanine dye stuffs, and trace nutrients, such as salts of iron, manganese boron, copper, cobalt, molybdenum and zinc.

The formulations in general contain from 0.1 to 95 per cent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricide, nematicide, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.001 and 5 kg of active compound per hectare of soil surface, preferably between 0.01 and 2 kg per ha.

The preparation and use of the active compounds according to the invention can be seen from the following examples.

Synthesis Example 1

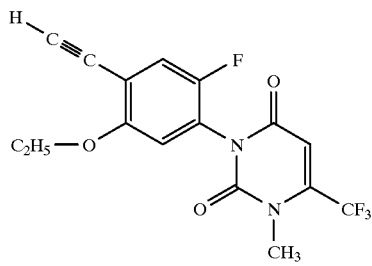

3-{5-Ethoxy-2-fluoro-4-[2-(trimethylsilyl)-1-ethynyl]phenyl}-1-methyl-6-trifluoromethyl-2,4(1H-,3H)-pyrimidinedione (1.37 g) was dissolved in ethanol (14 ml). To this solution, an aqueous solution (1 ml) of potassium fluoride (0.30 g) was added dropwise at room temperature and the mixture was stirred for further 8 hours. After the reaction, ethanol was distilled off under reduced pressure, extracted with ethyl acetate, washed with water, and then dried over anhydrous magnesium sulfate. Then, ethyl acetate was distilled off and the resulting oily substance was purified by chromatography on silica gel (ethyl acetate: n-hexane= 1:3) to obtain the objective 3-[5-ethoxy-4-(1-ethynyl)-2-fluorophenyl]-1-methyl-6-trifluoromethyl-2,4(1H,3H)-pyrimidinedione (0.94 g).

melting point: 139.5–140.5° C.

Synthesis Example 2

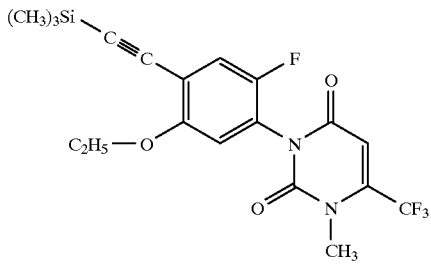

3-(4-Bromo-5-ethoxy-2-fluorophenyl)-1-methyl-6-trifluoromethyl-2,4(1H,3H)-pyrimidinedione (1.59 g), trimethylsilylacetylene (0.76 g), a palladium chloride-ditriphenylphosphine complex (136 mg) and copper(I) iodide (35 mg) were suspended in triethylamine (15 ml), and the mixture was stirred at 50° C. for 5 hours. After the reaction, triethylamine was distilled off under reduced pressure. Then, ethyl acetate was added thereto and insolubles were filtered. Ethyl acetate was distilled off and the resulting residue was purified by chromatography on silica gel (ethyl acetate: n-hexane=1:3 v/v) to obtain the objective 3-{5-ethoxy-2-fluoro-4-[2-(trimethylsilyl)-1-ethynyl]phenyl}-1-methyl-6-trifluoromethyl-2,4(1H,3H)-pyrimidinedione (1.48 g).

melting point: 98–101° C.

Synthesis Example 3

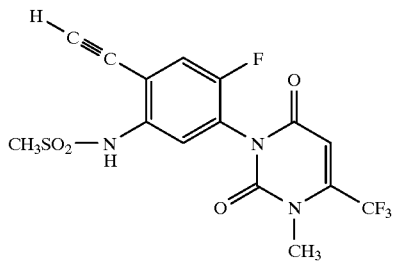

N-{5-[3,6-dihydro-2,6-dioxo-3,5-dimethyl-4-trifluoromethyl-1(2H)-pyrimidinyl]-4-fluoro-2-[2-(trimethylsilyl)-1-ethynyl]phenyl}methanesulfonamide (0.84 g) was dissolved in ethanol (7.5 ml). To this solution, an aqueous solution (0.6 ml) of potassium fluoride (0.16 g) was added dropwise, and the mixture was stirred for further 8 hours. After the reaction, ethanol was distilled off under reduced pressure, extracted with ethyl acetate, washed with water, and then dried over anhydrous magnesium sulfate. Ethyl acetate was distilled off and the resulting oily substance was purified by chromato-graphy on silica gel (ethyl acetate : n-hexane=1:3 v/v) to obtain the objective N-{5-[3,6-dihydro-2,6-dioxo-3,5-dimethyl-4-trifluoromethyl-1(2H)-pyrimidinyl]-2-(1-ethynyl)-4-fluorophenyl}methanesulfonamide (0.40 g).

melting point: 207–208° C.

Synthesis Example 4

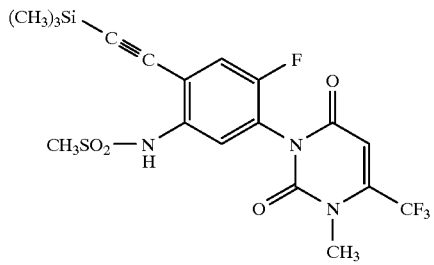

3-{5-Amino-2-fluoro-4-[2-(trimethylsilyl)-1-ethynyl]phenyl}-1,5-dimethyl-6-trifluoromethyl-2,4(1H,3H)-pyrimidinedione (2.07 g) was dissolved in pyridine (25 ml). To this solution, methanesulfonyl chloride (0.63 g) was added dropwise at 0° C. in such a manner that the inner temperature did not exceed 10° C., and the mixture was stirred at room temperature for further 12 hours. After the reaction, pyridine was distilled off under reduced pressure, extracted with methylene chloride, washed with diluted hydrochloric acid and water, and then dried over anhydrous magnesium sulfate. Methylene chloride was distilled off to obtain crude crystals (2.53 g) of the objective N-{5-[3,6-dihydro-2,6-dioxo-3,5-dimethyl-4-trifluoromethyl-1(2H)-pyrimidinyl]-4-fluoro-2-[2-(trimethylsilyl)-1-ethynyl]phenyl}-methanesulfonamide. Without being purified, this was used for the reaction of Synthesis Example 3.

Synthesis Example 5

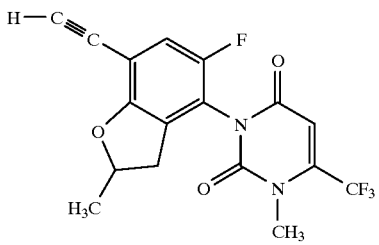

3-{5-Fluoro-2-methyl-7-[2-(trimethylsilyl)-1-ethynyl]-2,3-dihydrobenzo[b]furan-4-yl}-1-methyl-6-trifluoromethyl-2,4(1H,3H)-pyrimidinedione (0.39 g) was dissolved in ethanol (4 ml). To this solution, an aqueous solution (0.3 ml) of potassium fluoride (84 mg) was added dropwise at room temperature, and the mixture was stirred for further 8 hours. After the reaction, ethanol was distilled off under reduced pressure, extracted with ethyl acetate, washed with water, and then dried over anhydrous magnesium sulfate. Ethyl acetate was distilled off and the resulting oily substance was purified by chromatography on silica gel (ethyl acetate: n-hexane=1:3 v/v) to obtain the objective 3-[7-(1-ethynyl)-5-fluoro-2-methyl-2,3-dihydrobenzo[b]furan-4-yl]-1-methyl-6-trifluoromethyl-2,4(1H,3H)-pyrimidinedione (0.26 g).

melting point: 69–72.5° C.

Synthesis Example 6

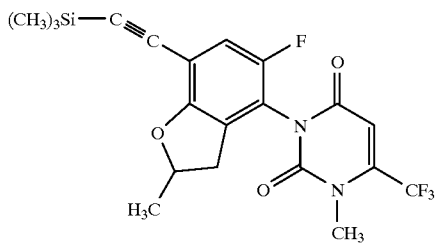

3-(7-Bromo-5-fluoro-2-methyl-2,3-dihydrobenzo[b]furan-4-yl)-1-methyl-6-trifluoromethyl-2,4(1-3H)-pyrimidinedione (1.15 g), trimethylsilylacetylene (0.53 g), a palladium chloride-ditriphenylphospline complex (95 mg) and copper(I) iodide (27 mg) was suspended in triethylamine (11 ml) and DMF (3 ml), and the mixture was stirred at 50° C. for 12 hours. After the reaction, triethylamine was distilled off under reduced pressure. Ethyl acetate was added thereto, and the insolubles were filtered. Then, ethyl acetate was distilled off, and the resulting residue was purified by chromatography on silica gel (ethyl acetate: n-hexane=1:3 v/v) to obtain the objective 3-{5-fluoro-2-methyl-7-[2-(trimethylsilyl)-1-ethynyl]-2,3-dihydrobenzo[b]furan-4-yl}-1-methyl-6-trifluoromethyl-2,4(1H,-3H)-pyrimidinedione (0.40 g).

Table 2 shows the compounds obtained in the above Synthesis Examples 1 to 6, together with the compounds obtained in the same way as the Synthesis Examples 1 to 6.

TABLE 2

| Compound No. | R | X | Y | Zn | $R^2$ | melting point (°C.) or refractive index ($n_D^{20}$) |
|---|---|---|---|---|---|---|
| 1 | H | F | H | H | $CH_2CH_2CH_2F$ | 92–93 |
| 2 | $Si(CH_3)_3$ | F | H | H | $CH_2CH_2CH_2F$ | 1.545 |

| Compound No. | R | X | Y | Zn | $R^2$ | $R^3$ | $R^4$ | melting point (°C.) or refractive index ($n_D^{20}$) |
|---|---|---|---|---|---|---|---|---|
| 3 | H | F | $OCH_3$ | H | $CF_3$ | $CH_3$ | $CH_3$ | 65–68 |
| 4 | H | F | O-cyclopentyl | H | $CF_3$ | H | $CH_3$ | 155–155.5 |
| 5 | H | H | H | H | $CF_3$ | H | $CH_3$ | 176–177 |
| 6 | H | F | $NHSO_2CH_3$ | H | $CF_3$ | $CH_3$ | $CH_3$ | 207–208 |
| 7 | H | F | 5-OCH($CH_3$)$CH_2$-6 | | $CF_3$ | H | $CH_3$ | 68–72.5 |
| 8 | H | F | $OCH_3$ | H | $CF_3$ | H | $CH_3$ | 59–61 |
| 9 | $Si(CH_3)_3$ | H | H | H | $CF_3$ | H | $CH_3$ | 182.5–194 |
| 10 | $Si(CH_3)_3$ | F | O-cyclopentyl | H | $CF_3$ | H | $CH_3$ | 140–142 |
| 11 | $Si(CH_3)_3$ | F | $OC_2H_5$ | H | $CF_3$ | H | $CH_3$ | 98–101 |
| 12 | H | F | $OC_2H_5$ | H | $CF_3$ | H | $CH_3$ | 139.5–140.5 |
| 13 | H | Cl | H | H | $CF_3$ | H | $CH_3$ | 151–152.5 |
| 14 | $C(CH_3)_3$ | Cl | H | H | $CF_3$ | H | $CH_3$ | 118.5–119.5 |

TABLE 2-continued

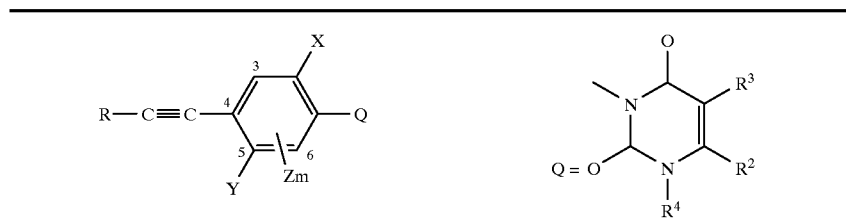

| Compound No. | R | X | Y | Zn | R² | R³ | R⁴ | melting point (°C.) or refractive index ($n_D^{20}$) |
|---|---|---|---|---|---|---|---|---|
| 15 | CH₂CH₂CH₂CH₃ | Cl | H | H | CF₃ | H | CH₃ | 1.545 |
| 16 | C(CH₃)₃ | Cl | H | H | CF₃ | H | CH₃ | 141–142.5 |
| 17 | H | F | NHSO₂CH₃ | H | CF₃ | H | CH₃ | 69–71.5 |
| 18 | H | F | OSO₂CH₃ | H | CF₃ | H | CH₃ | 206–207 |
| 19 | H | F | N(SO₂CH₃)₂ | H | CF₃ | H | CH₃ | 255.5–256.5 |
| 20 | H | F | NO₂ | H | CF₃ | H | CH₃ | 191–192 |
| 21 | H | F | OCH(CH₃)₂ | H | CF₃ | CH₃ | CH₃ | 125–126.5 |
| 22 | Si(CH₃)₃ | F | NO₂ | H | CF₃ | CH₃ | CH₃ | 152–154 |
| 23 | H | F | NO₂ | H | CF₃ | CH₃ | CH₃ | 66–68 |
| 24 | Si(CH₃)₃ | F | NH₂ | H | CF₃ | CH₃ | CH₃ | 192–198 |
| 25 | H | F | NH₂ | H | CF₃ | CH₃ | CH₃ | 179–182 |
| 26 | H | F | H | H | CF₃ | CH₃ | CH₃ | 154.5–155 |
| 27 | Si(CH₃)₃ | F | H | H | CF₃ | CH₃ | CH₃ | 131.5–132.5 |
| 28 | H | H | OCF₃ | H | CF₃ | H | CH₃ | 124–125 |
| 29 | Si(CH₃)₃ | H | OCF₃ | H | CF₃ | H | CH₃ | 96–98 |
| 30 | H | F | OCF₂CHFCl | H | CF₃ | H | CH₃ | 1.5068 |
| 31 | Si(CH₃)₃ | H | CO₂C₂H₅ | H | CF₃ | H | CH₃ | 139 |
| 32 | H | H | CO₂C₂H₅ | H | CF₃ | H | CH₃ | 126–127 |
| 33 | Si(CH₃)₃ | H | OCH₂CH₂CH₃ | H | CF₃ | H | CH₃ | 63–65 |
| 34 | Si(CH₃)₃ | F | OCF₃ | H | CF₃ | H | CH₃ | 1.4969 |
| 35 | Si(CH₃)₃ | F | NHCOCH₃ | H | CF₃ | CH₃ | CH₃ | 89–96 |
| 36 | H | F | OCF₃ | H | CF₃ | H | CH₃ | 1.5075 |
| 37 | H | F | NHCOCH₃ | H | CF₃ | CH₃ | CH₃ | 230–231 |
| 38 | H | F | OCH₂CH₂CH₃ | H | CF₃ | H | CH₃ | 120–122 |

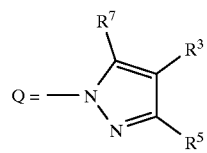

| Compound No. | R | X | Y | Zn | R³ | R⁵ | R⁷ | melting point (°C.) or refractive index ($n_D^{20}$) |
|---|---|---|---|---|---|---|---|---|
| 39 | Si(CH₃)₃ | F | OCH₃ | H | CN | H | NH₂ | 172–173 |
| 40 | H | F | OCH₃ | H | CN | H | NH₂ | 250 or more |

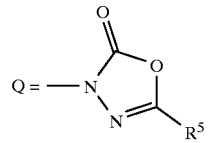

| Compound No. | R | X | Y | Zn | R⁵ | melting point (°C.) or refractive index ($n_D^{20}$) |
|---|---|---|---|---|---|---|
| 41 | H | F | OCH₃ | H | C(CH₃)₃ | 226 |
| 42 | Si(CH₃)₃ | F | OCH₃ | H | C(CH₃)₃ | 1.5372 |

TABLE 2-continued

Structure: R—C≡C—[benzene ring with positions 3(X), 4, 5(Y), 6, Zm, Q]

Q = tetrazolinone:

| Compound No. | R | X | Y | Zn | R² | melting point (°C.) or refractive index (n_D^20) |
|---|---|---|---|---|---|---|
| 43 | H | F | N(SO₂C₂H₅)₂ | H | CH₂CH₂CH₂F | 143–148 |
| 44 | Si(CH₃)₃ | F | N(SO₂C₂H₅)₂ | H | CH₂CH₂CH₂F | 42–45 |
| 45 | Si(CH₃)₃ | F | NH₂ | H | CH₂CH₂CH₂F | 112–113 |
| 46 | Si(CH₃)₃ | F | NO₂ | H | CH₂CH₂CH₂F | 85–90 |
| 47 | H | F | NHSO₂C₂H₅ | H | CH₂CH₂CH₂F | 1.5752 |

Q = uracil structure with R², R³, R⁴:

| Compound No. | R | X | Y | Zn | R² | R³ | R⁴ | melting point (°C.) or refractive index (n_D^20) |
|---|---|---|---|---|---|---|---|---|
| 48 | H | F | SO₂CH₃CH₃ | H | CF₃ | H | CH₃ | 208 |
| 49 | Si(CH₃)₃ | F | H | H | CF₃ | H | CH₃ | 136–138 |
| 50 | Si(CH₃)₃ | F | NO₂ | H | CF₃ | H | CH₃ | 161–165 |
| 51 | Si(CH₃)₃ | F | N(COC(CH₃)₃)SO₂CH₃ | H | CF₃ | H | CH₃ | 225–227 |
| 52 | H | F | N(COC(CH₃)₃)SO2C₂H₅ | H | CF₃ | H | CH₃ | 197–199 |
| 53 | H | F | N(COCH₃)SO2C₂H₅ | H | CF₃ | H | CH₃ | 72–77 |
| 54 | Si(CH₃)₃ | F | NHSO₂CH₂CH₃ | H | CF₃ | H | CH₃ | 171–172 |
| 55 | H | F | OCH₂CH(CH₃)₂ | H | CF₃ | H | CH₃ | 48–57 |
| 56 | H | F | OH | H | CF₃ | H | CH₃ | 86–90 |
| 57 | H | F | O-cyclobutyl | H | CF₃ | H | CH₃ | 56–66 |
| 58 | CH₂OH | F | OCH₃ | H | CF₃ | H | CH₃ | 73–79 |

| Compound No. | R | X | Y | Zn | R² | R³ | R⁴ | melting point (°C.) or refractive index (n_D^20) |
|---|---|---|---|---|---|---|---|---|
| 59 | H | F | OCH₂CH=CH₂ | H | CF₃ | H | CH₃ | 103–104 |
| 60 | H | F | OCH₂C≡CH | H | CF₃ | H | CH₃ | 56–59 |
| 61 | H | F | OCH₂OCH₃ | H | CF₃ | H | CH₃ | 49–56 |
| 62 | Si(CH₃)₃ | F | OCH₂OCH₃ | H | CF₃ | H | CH₃ | 72–77 |
| 63 | Si(CH₃)₃ | F | OH | H | CF₃ | H | CH₃ | 81–86 |
| 64 | H | F | OCH₂C(CH₃)=CH₂ | H | CF₃ | H | CH₃ | 102–105 |
| 65 | H | F | OCH₂CH₂F | H | CF₃ | H | CH₃ | 62–66 |
| 66 | H | F | OCH₂CH₂CH₂F | H | CF₃ | H | CH₃ | 75–79 |
| 67 | H | F | OCH(CH₃)₂ | H | CF₃ | H | CH₃ | 68–80 |
| 68 | H | F | OCH₂CH₂CH₂CH₃ | H | CF₃ | H | CH₃ | 1.5328 |
| 69 | H | F | H | H | CF₃ | H | CH₃ | 149–151 |
| 70 | H | F | N(COC(CH₃)₃)SO₂CH₃ | H | CF₃ | CH₃ | CH₃ | 235–236 |
| 71 | H | F | NHSO₂CH₂CH₃ | H | CF₃ | H | CH₃ | 78–85 |
| 72 | H | F | SCH₃ | H | CF₃ | H | CH₃ | 136–138 |
| 73 | H | F | S-cyclopentyl | H | CF₃ | H | CH₃ | 122–125 |
| 74 | Si(CH₃)₃ | F | SCH₃ | H | CF₃ | H | CH₃ | 64–70 |
| 75 | Si(CH₃)₃ | F | S-cyclopentyl | H | CF₃ | H | CH₃ | 48–54 |
| 76 | H | F | OCH₂CO₂CH₃ | H | CF₃ | H | CH₃ | 139–140 |
| 77 | Si(CH₃)₃ | F | OCH₂CO₂CH₃ | H | CF₃ | H | CH₃ | 55–63 |

TABLE 2-continued

| 78 | H | F | SO$_2$-cyclopentyl | H | CF$_3$ | H | CH$_3$ | 175–177 |
| 79 | H | F | SCH$_2$CH$_3$ | H | CF$_3$ | H | CH$_3$ | 91–93 |
| 80 | Si(CH$_3$)$_3$ | F | SCH$_2$CH$_3$ | H | CF$_3$ | H | CH$_3$ | 1.5513 |

SYNTHESES OF INTERMEDIATES

Synthesis Example 7

(Synthesis of the starting material for Synthesis Example 2)

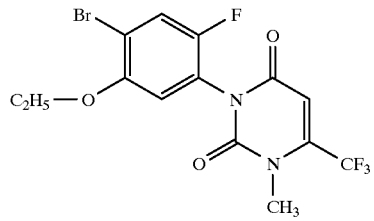

3-(4-Bromo-5-ethoxy-2-fluorophenyl)-6-trifluoromethyl-2,4(1H,3H)-pyrimidinedione (2.38 g), methyl iodide (1.06 g) and potassium carbonate (1.04 g) were suspended in DMF (12 ml), and the mixture was stirred at room temperature for about 8 hours. After the reaction, DMF was distilled off under reduced pressure, extracted with ethyl acetate, washed with water, and dried over anhydrous magnesium sulfate. Then, ethyl acetate was distilled off, and the resulting residue was crystallized from a mixed solvent of ethyl acetate and n-hexane (1:5 v/v) to obtain the objective 3-(4-bromo-5-ethoxy-2-fluorophenyl)-1-methyl-6-trifluoromethyl-2,4(1H,3H)-pyrimidinedione (2.08 g).
melting point: 127–127.5° C.

Synthesis Example 8

(Synthesis of the starting material for Synthesis Example 7)

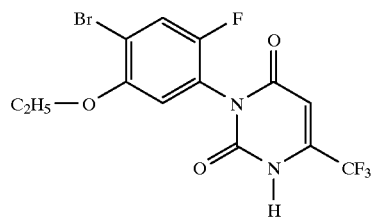

Ethyl 3-amino-4,4,4-trifluorocrotonate (3.42 g) was dissolved in DMF (19 ml). To this solution, a suspension of sodium methoxide (1.10 g) in DMF was added dropwise at 5° C., and the mixture was stirred at 5° C. for 30 minutes. Then, a DMF solution of ethyl N-(4-bromo-5-ethoxy-2-fluorophenyl)-carbamate was added dropwise thereto, and the mixture was stirred at 130° C. for 4 hours. After the reaction, DMF was distilled off under reduced pressure. Then, the residue was acidified by adding diluted hydrochloric acid thereto. This was extracted with ethyl acetate, washed with water, and dried over anhydrous magnesium sulfate. Then, ethyl acetate was distilled off, and the resulting residue was crystallized from a mixed solvent of ethyl acetate and n-hexane (1:3 v/v) to obtain the objective 3-(4-bromo-5-ethoxy-2-fluorophenyl)-6-trifluoromethyl-2,4(1H,3H)-pyrimidinedione (3.63 g).

melting point: 161–162.5 ° C.

Synthesis Example 9

(Synthesis of the starting material for Synthesis Example 8)

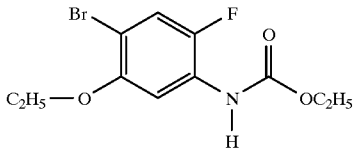

Ethyl chloroformate (2.15 g) was added dropwise to a solution of 4-bromo-5-ethoxy-2-fluoroaniline (4.21 g) and pyridine (2.84 g) in methylene chloride (36 ml) at 0° C., and the mixture was stirred at 10° C. for 3 hours. After the reaction, this was extracted with methylene chloride, then washed with diluted hydrochloric acid and an aqueous sodium hydrogencarbonate solution, and dried over anhydrous magnesium sulfate. Then, methylene chloride was distilled off, and the resulting crude crystals were crystallized from a mixed solvent of ethyl acetate and n-hexane (1:5 v/v) to obtain the objective ethyl N-(4-bromo-5-ethoxy-2-fluorophenyl)carbamate (5.30 g).

melting point: 92.5–95° C.

Synthesis Example 10

(Synthesis of the starting material for Synthesis Example 9)

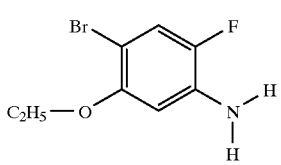

5-Amino-2-bromo-4-fluorophenol (10.30 g), ethyl iodide (9.36 g) and potassium carbonate (7.59 g) were suspended in acetonitrile (100 ml), and the mixture was heated under refluxing for about 6 hours. After the reaction, the precipitates were filtered, the solvent was distilled off, extracted with ethyl acetate, and dried over anhydrous magnesium sulfate. Then, ethyl acetate was distilled off, and the resulting oily substance was purified by chromatography on silica gel (ethyl acetate n-hexane=1:3 v/v) to obtain the objective 4-bromo-5-ethoxy-2-fluoroaniline (7.93 g). $n_D^{20}$=1.3579

Synthesis Example 11

(Synthesis of the starting material for Synthesis Example 4)

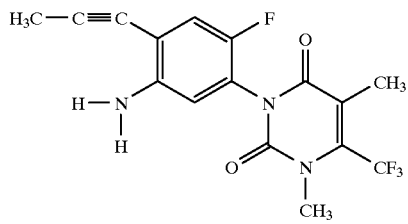

A mixture consisting of 3-{2-fluoro-5-nitro-4-[2-(trimethylsilyl)-1-ethynyl]phenyl}-1,5-dimethyl-6-trifluoromethyl-2,4(1H,3H)-pyrimidinedione (11.95 g), iron powder (15.68 g), acetic acid (14 ml), water (14 ml) and ethanol (280 ml) was heated to 80° C. and stirred for 3 hours. Then, the solvent was distilled off under reduced pressure. An aqueous sodium hydroxide solution was added thereto to make it alkaline. Then, methylene chloride was added thereto for extraction. After washing with water, it was dried over anhydrous magnesium sulfate. Then, methylene chloride was distilled off, and the resulting residue was crystallized from a mixed solvent of ethyl acetate and n-hexane (1:3 v/v) to obtain 3-{5-amino-2-fluoro-4-[2-(trimethylsilyl)-1-ethynyl]-phenyl}-1,5-dimethyl-6-trifluoromethyl-2,4(1H,3H)-pyrimidinedione (7.70 g).

melting point: 192–198° C.

Synthesis Example 12

(Synthesis of the starting material for Synthesis Example 11)

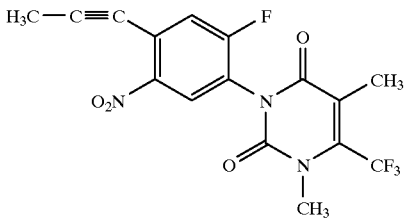

3-(4-Bromo-2-fluoro-5-nitrophenyl)-1,5-dimethyl-6-trifluoromethyl-2,4(1H,3H) pyrimidinedione (12.85 g), trimethylsilylacetylene (5.93 g), a palladium chloride-ditriphenylphosphine complex (1.06 g) and copper(I) iodide (0.302 g) were suspended in triethylamine (210 ml), and the mixture was stirred at room temperature for 5 hours. After the reaction, triethylamine was distilled off under reduced pressure. Ethyl acetate was added thereto, and insolubles were filtered. Then, ethyl acetate was distilled off, and the resulting residue was purified by chromatography on silica gel (ethyl acetate : n-hexane=1:3) to obtain the objective 3-{2-fluoro-5-nitro-4-[2-(trimethylsilyl)-1-ethynyl] phenyl}-1,5-dimethyl-6-trifluoromethyl-2,4(1H,3H)-pyrimidinedione (11.63 g).

melting point: 152–154° C.

Synthesis Example 13

(Synthesis of the starting material for Synthesis Example 12)

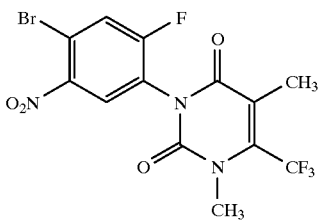

3-(4-Bromo-2-fluorophenyl)-1,5-dimethyl-6-trifluoromethyl-2,4(1H,3H)-pyrimidinedione (14.79 g) was dissolved in concentrated sulfuric acid (190 ml). To this solution, fuming nitric acid (2.69 g) was added dropwise at 0° C. in such a manner that the inner temperature did not exceed 10° C., and the mixture was stirred 10° C. for further 5 hours.

The reaction mixture was poured into ice water, and extracted with methylene chloride. After washing with water, it was dried over anhydrous magnesium sulfate. Then, methylene chloride was distilled off to obtain the objective 3-(4-bromo-2-fluoro-5-nitrophenyl)-1,5-dimethyl-6-trifluoromethyl-2,4(1H,3H)-pyrimidinedione (16.44 g). Without being purified, this was used for a subsequent reaction.

Synthesis Example 14

(Synthesis of the Starting Material for Synthesis Example 13)

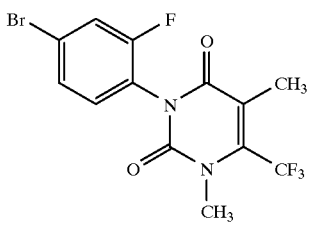

3-(4-Bromo-2-fluorophenyl)-S-methyl-6-trifluoromethyl-2,4(1H,3H)-pyrimidinedione (16.52 g), methyl iodide (7.99 g) and potassium carbonate (7.76 g) were suspended in DMF (90 ml), and the mixture was stirred at room temperature for about 8 hours. After the reaction, DMF was distilled off under reduced pressure, extracted with ethyl acetate, washed with water, and dried over anhydrous magnesium sulfate. Ethyl acetate was distilled off, and the resulting residue was crystallized from a mixed solvent of ethyl acetate and n-hexane (1:3 v/v) to obtain the objective 3-(4-bromo-2-fluoro-phenyl)-1,5-dimethyl-6-trifluoromethyl-2,4(1H,3H)-pyrimidinedione (14.92 g).

melting point: 129–131° C.

Synthesis Example 15

(Synthesis of the starting material for Synthesis Example 14)

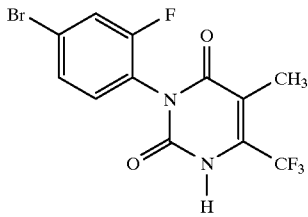

Ethyl 3-amino-4,4,4-trifluoro-2-methylcrotonate (26.0 g) was dissolved in DMF (123 ml). To this solution, a suspension of sodium methoxide in DMF (7.78 g) was added dropwise at 0° C., and the mixture was stirred at 5° C. for 30 minutes. Then, a DMF solution of ethyl N-(4-bromo-2-fluoro-phenyl)carbamate (31.44 g) was added dropwise thereto, and the mixture was stirred at 130° C. for 5 hours. After the reaction, DMF was distilled off under reduced pressure, and the residue was acidified by adding diluted hydrochloric acid thereto. This was extracted with ethyl acetate, washed with water, and then dried over anhydrous magnesium sulfate. Ethyl acetate was distilled off, and the resulting residue was crystallized from ethyl acetate—n-hexane (1:3 v/v) to obtain the objective 3-(4-bromo-2-fluorophenyl)-5-methyl-6-trifluoromethyl-2,4(1H,3H)-pyrimidinedione (18.78 g).

melting point: 187.5–189° C.

Synthesis Example 16

(Synthesis of the starting material for Synthesis Example 15)

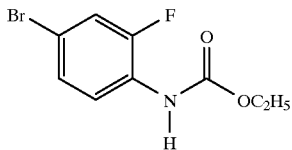

Ethyl chloroformate (15.91 g) was added dropwise to a solution of 4-bromo-2-fluoroaniline (25.33 g) and pyridine (21.06 g) in methylene chloride (260 ml) at 0° C., and the mixture was stirred at 10° C. for 3 hours. After the reaction, it was extracted with methylene chloride, then washed with diluted hydrochloric acid and an aqueous sodium hydrogencarbonate solution, and dried over anhydrous magnesium sulfate. Then, methylene chloride was distilled off, and the resulting crude crystals were crystallized from ethyl acetate—n-hexane (1:5 v/v) to obtain the objective ethyl N-(4-bromo-2-fluorophenyl)carbamate (34.45 g).

melting point: 72–73° C.

Synthesis Example 17

(Synthesis of the starting material for Synthesis Example 6)

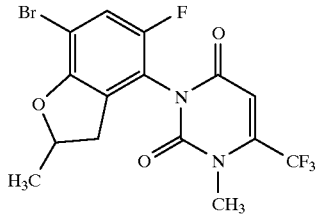

3-(2-Allyl-4-bromo-6-fluoro-3-hydroxyphenyl)-1-methyl-6-trifluoromethyl-2,4(1H,3H)-pyrimidine-dione (1.50 g) was dissolved in xylene (15 ml). After p-toluenesulfonic acid monohydrate (0.54 g) was added thereto, it was allowed to react under the refluxing condition for 12 hours. After the completion of the reaction, it was extracted with ethyl acetate, washed with an aqueous sodium hydrogencarbonate solution and water, and then dried over anhydrous magnesium sulfate. Ethyl acetate was distilled off, and the resulting oily substance was purified by chromatography on silica gel (ethyl acetate:n-hexane=1:3) to obtain the objective 3-(7-bromo-5-fluoro-2-methyl-2,3-dihydro-benzo[b]furan-4-yl)-1-methyl-6-trifluoromethyl-2,4(1H,3H)-pyrimidinedione (1.46 g).

melting point: 66–75.5° C.

Synthesis Example 18

(Synthesis of the starting material for Synthesis Example 17)

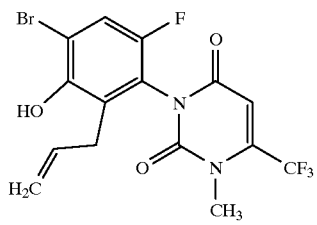

3-(5-Allyloxy-4-bromo-2-fluorophenyl)-1-methyl-6-trifluoromethyl-2,4(1H,3H)-pyrimidinedione (3.17 g) was dissolved in N, N-diethylaniline (11 ml) and allowed to react at 210° C. for 2.5 hours. After the completion of the reaction, the reaction solution was poured into water, and diluted hydrochloric acid was added thereto for acidification. It was extracted with ethyl acetate, washed with water, and then dried over anhydrous magnesium sulfate. Ethyl acetate was distilled off, and the resulting oily substance was purified by chromatography on silica gel (ethyl acetate : n-hexane=1:2 v/v) to obtain the objective 3-(2-allyl-4-bromo-6-fluoro-3-hydroxyphenyl)-1-methyl-6-trifluor-omethyl-2,4(1H,3H)-pyrimidinedione (2.57 g).

$n_D^{20}$=1.5491

Synthesis Example 19

(Synthesis of the starting material for Synthesis Example 18)

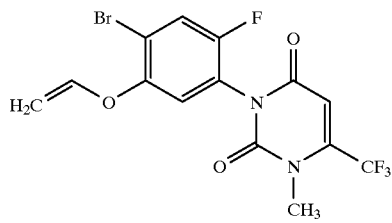

A crude product (16.67 g) of 3-(5-allyloxy-4-bromo-2-fluorophenyl)-6-trifluoromethyl-2,4(1H,3H)-pyrimidinedione, methyl iodide (7.18 g) and potassium carbonate (7.03 g) were suspended in DMF (80 ml), and the mixture was stirred at room temperature for 8 hours. After the reaction, DMF was distilled off under reduced pressure, extracted with ethyl acetate, washed with water, and dried over anhydrous magnesium sulfate. Then, ethyl acetate was distilled off, and the resulting oily substance was purified by chromatography on silica gel (ethyl acetate: n-hexane=1:3 v/v), and the resulting oily substance was crystallized from ethyl acetate—n-hexane to obtain the objective 3-(5-allyloxy4-bromo-2-fluorophenyl)-1-methyl-6-trifluoromethyl-2,4(1H,3H)-pyrimidinedione (5.42 g).

melting point: 123.5–124° C.

Synthesis Example 20

(Synthesis of the starting material for Synthesis Example 19)

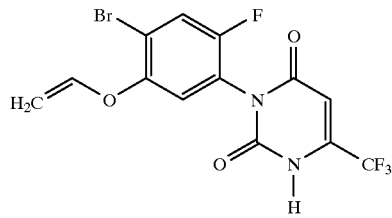

Ethyl 3-amino-4,4,4-trifluorocrotonate (9.66 g) was dissolved in DMF (53 ml). To this solution, a suspension of sodium methoxide (3.11 g) in DMF was added dropwise, and the mixture was stirred at 5° C. for 30 minutes. Then, a DMF solution of ethyl N-(5-allyloxy-4-bromo-2-fluorophenyl)carbamate was added dropwise thereto, and the mixture was stirred at 130° C. for 5 hours. After the reaction, DMF was distilled off under reduced pressure, and the residue was acidified by adding diluted hydrochloric acid thereto. This was extracted with ethyl acetate, washed with water, and then dried over anhydrous magnesium sulfate. Then, ethyl acetate was distilled off to obtain an oily substance (18.98 g) containing the objective 3-(5-allyloxy-4-bromo-2-fluorophenyl)-6-trifluoromethyl-2,4(1H,3H)-pyrimidinedione. Without being purified, this was used for the reaction of Synthesis Example 19.

Synthesis Example 21

(Synthesis of the starting material for Synthesis Example 20)

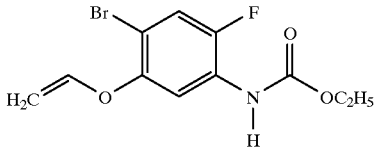

Ethyl chloroformate (5.97 g) was added dropwise to a solution of 5-allyloxy4-bromo-2-fluoroaniline (12.3 g) and pyridine (7.90 g) in methylene chloride (100 ml) at 0° C., and the mixture was stirred at 10° C. for 3 hours. After the reaction, this was extracted with methylene chloride, then washed with diluted hydrochloric acid and an aqueous sodium hydrogencarbonate solution, and dried over anhydrous magnesium sulfate. Then, methylene chloride was distilled off to obtain to the objective ethyl N-(5-allyloxy-4-bromo-2-fluorophenyl)carbamate (15.67 g).

melting point: 66–68° C.

Synthesis Example 22

(Synthesis of the starting material for Synthesis Example 2 1)

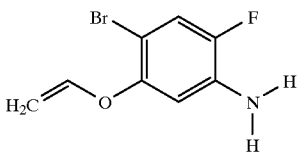

5-Amino-2-bromo-4-fluorophenol (30.9 g), allyl bromide (21.8 g) and potassium carbonate (22.77 g) were suspended in acetonitrile (300 ml), and the mixture was stirred at room temperature for 12 hours. After the reaction, the precipitates were filtered, the solvent was distilled off, and this was extracted with ethyl acetate. After washing with water, it was dried over anhydrous magnesium sulfate. Then, ethyl acetate was distilled off and the resulting oily substance was purified by chromatography on silica gel (ethyl acetate: n-hexane=1:3) to obtain the objective 5-allyloxy-4-bromo-2-fluoroaniline (12.14 g).

BIOLOGICAL TEST EXAMPLES

Test Example 1

(Test of pre-emergence soil-treatment)

Preparations of active compounds carrier (acetone): 5 parts by weight emulsifier (benzyloxy polyglycol ether): 1 part by weight A preparation of active compound is obtained as an emulsion by mixing one part by weight of an active compound, the above-stated amount of carrier and the above-stated amount of emulsifier. A prescribed amount of this preparation is diluted with water to prepare a testing solution.

Testing procedure

In the greenhouse, seeds of *Echinochloa crus-galli* Beauv., *Setaria viridis* Beauv., *Amaranthus lividus* and

*Persicaria lapathifolia* were sowed each in the surface layer of plowed land soil filled in a 120 cm² pot with soil-covering, and each a prescribed amount of the testing solution prepared by the above method was uniformly spread on the surface layer of soil in the testing pot. The herbicidal effect was examined on the day after 4 weeks from the spreading.

In this test, for example, the above compounds Nos. 3, 4, 5, 6, 7, 8, 12, 17, 18, 26, 30, 31, 52, 53, 54, 59, 60, 61, 62, 64, 65 and 66 of the invention exhibited 95% or more of the herbicidal rate against *Echinochloa crus-galli* Beauv., *Setaria viridis* Beauv., *Amaranthus lividus* and *Persicaria lapathifolia* by the dose of 0.5 kg/ha.

Test Example 2

(Test offoliage-treatment)

In the greenhouse, seeds of *Echinochloa crus-galli* Beauv., *Setaria viridis* Beauv., *Amaranthus lividus* and *Persicaria lapathifolia* were sowed each in a 120 cm² pot filled with plowed land soil and covered with soil. After 10 days from the sowing and soil-covering (when the weeds were in 2-leaf stage on average), each a prescribed amount of the testing solution prepared similarly to those in the above Test Example 1 was uniformly spread on the foliage part of tested plant in the testing pot. After 3 weeks from the spreading, the herbicidal effect was examined.

In this test, for example, the above compounds Nos. 3, 4, 7, 8, 12, 17, 26, 30, 31, 52, 53, 54, 59, 60, 61, 62, 64, 65 and 66 of the invention exhibited 95% or more of the herbicidal rate against *Echinochloa crus-galli, Setaria viridis, Amaranthus lividus* and *Persicaria lapathifolia* by the dose of 0.5 kg/ha.

We claim:
1. Phenylacetylene derivatives of formula:

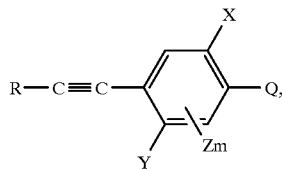

(I)

wherein
X represents hydrogen, halogen, $C_{1-6}$ alkyl, or $C_{1-6}$ haloalkyl, Y represents hydrogen, hydroxy, halogen, cyano, nitro, $C_{1-6}$ alkyl, $C_{1-6}$ haloalkyl, $C_{1-6}$ alkoxy, $C_{3-8}$ cycloalkoxy, $C_{1-6}$ haloalkoxy, $C_{1-3}$ alkoxy-$C_{1-3}$ alkoxy, $C_{1-6}$-alkylthio, $C_{3-8}$ cycloalkylthio, $C_{1-6}$ haloalkylthio, $C_{1-6}$ alkylsulfinyl, $C_{1-6}$ alkylsulfonyl, $C_{3-8}$ cycloalkylsulfonyl $C_{1-6}$ haloalkylsufonyl, $C_{1-6}$ alkylsulfonyloxy, $C_{3-6}$ alkenyloxy, $C_{3-6}$ alkyloxy, a group $SO_2NR^aR^b$, a group $COOR^c$, a group $CONR^dR^e$, optionally substituted amino, a group $A^1\text{-}(CH_2)n\text{-}CHR^f\text{—}COOR^g$, $C_{1-3}$ alkoxycarbonyl-$C_{1-3}$ alkyl or $C_{1-3}$ alkoxycarbonyl-$C_{1-3}$ haloalkyl, or Y may form a 5- or 6-membered ring together with Z which is vicinal to the carbon atom of Y, $R^a$ and $R^b$ each represent independently hydrogen or $C_{1-6}$ alkyl or $R^a$ and $R^b$ may form together with the N atom to which they are bonded a 5- or 6-membered heterocyclic group, $R^c$ represents hydrogen, an alkali metal, an alkaline earth metal, $C_{1-6}$ alkyl or $C_{1-4}$ alkoxy-carbonyl-$C_{1-4}$ alkyl, $R^d$ represents hydrogen or $C_{1-6}$ alkyl, $R^e$ represents hydrogen or $C_{1-6}$ alkyl, $R^f$ represents hydrogen, halogen or $C_{1-6}$ alkyl, $R^g$ represents hydrogen, an alkali metal, an alkaline earth metal or $C_{1-6}$ alkyl, $A^1$ represents oxygen or sulfur, n is 0 or 1, Z represents hydrogen or halogen, m is 1 or 2, R represents hydrogen, halogen, $C_{1-6}$ alkyl, hydroxy-$C_{1-6}$ alkyl, tri($C_{1-6}$ alkyl)silyl, a group $COOR^c$ or a group $CONR^dR^e$, Q represents a heterocycle selected from the group consisting of

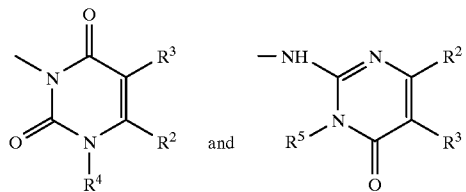

$R^2$ represents hydrogen or $C_{1-6}$ haloalkyl, $R^3$ represents hydrogen, cyano, halogen or $C_{1-6}$ allyl, $R^4$ represents hydrogen, amino or $C_{1-6}$ alkyl, $R^5$ represents hydrogen, $C_{1-6}$ alkyl, $C_{1-6}$ haloalkyl, $C_{3-8}$ cycloalkyl or $C_{3-8}$ alkynyl.

2. The phenylacetylene derivative of formula (I)

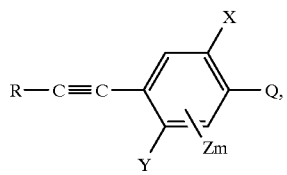

(I)

wherein
X represents hydrogen, fluorine, chlorine, methyl or trifluoromethyl,

Y represents hydrogen, hydroxy, fluorine, chlorine, cyano, nitro, methyl, ethyl, propyl, trifluoromethyl, chlorodifluoromethyl, $C_{1-3}$ alkoxy, $C_{3-6}$ cycloalkoxy, $C_{1-3}$ haloalkoxy, $C_{1-3}$ alkoxy-$C_{1-3}$ alkoxy, $C_{1-3}$ alkylthio, $C_{3-6}$ cycloalkylthio, $C_{1-3}$ haloalkylthio, $C_{1-3}$ alkyl-sulfinyl, $C_{1-3}$ alkyl-sulfonyl, $C_{3-6}$ cycloalkylsulfonyl, $C_{1-3}$ haloalkylsulfonyl, $C_{1-3}$ alkyl-sulfonyl-oxy, $C_{3-4}$ alkenyloxy, $C_{3-4}$ alkynyloxy, aminosulfonyl, methyl-aminosulfonyl ethylamino-sulfonyl, diethylaminosulfonyl, 1-pyrroli-dinyl-sulfonyl, a group $COOR^c$, aminocarbonyl, amino, acetylamino, trifluoromethylsulfonylamino, methylsulfonylamino, ethylsulfonylamino, bis(methylsulfonyl)amino, bis(ethylsulfonyl)amino, ($C_{1-4}$ alkylcarbonyl)($C_{1-4}$ alkyl-sufonyl)amino, $C_{1-3}$ alkoxycarbonyl-$C_{1-3}$ alkylthio, $C_{1-3}$ alkoxy-carbonyl-$C_{1-3}$ haloalkyl-thio, $C_{1-3}$ alkoxycarbonyl-$C_{1-3}$ alkoxy, $C_{1-3}$ alkoxy-carbonyl-$C_{1-3}$ haloalkoxy, $C_{1-3}$ alkoxycarbonyl-$C_{1-3}$-$C_{1-3}$ alkyl or $C_{1-3}$ alkoxycarbonyl-$C_{1-3}$ haloalkyl, $R^c$ represents hydrogen, methyl, ethyl, propyl, methoxycarbonylmethyl, ethoxycarbonylmethyl, 1-(methoxycarbonyl)ethyl or 1-(ethoxy-carbonyl)ethyl, Z represents hydrogen, fluorine or chlorine, or Y may form a group —OCR$^h$R$^i$—CH$_2$— or a group —OCR$^h$=CH— together with Z which is vicinal to the carbon atom of Y, $R^h$ represents hydrogen, $C_{1-3}$ alkyl, hydroxy-$C_{1-3}$ alkyl, $C_{1-3}$ alkoxy-$C_{1-3}$ alkyl, carboxy or $C_{1-3}$ alkoxycarbonyl, $R^i$ represents hydrogen or $C_{1-3}$ alkyl, m is 1 or 2, R represents hydrogen, fluorine, methyl hydroxymethyl, trimethylsilyl, methoxycarbonyl, ethoxycarbonyl or aminocarbonyl, Q represents a heterocycle selected from the group consisting of

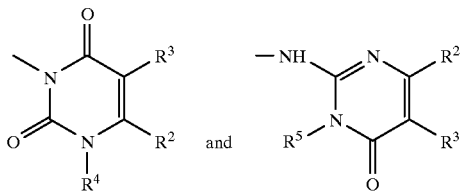

$R^2$ represents hydrogen, trifluoromethyl, difluoromethyl, chlorodifluoromethyl, 2,2,2-trifluoroethyl, 3-fluoropropyl, 3,3,3-trifluoropropyl, 2,2,3,3-tetrafluoropropyl or 1,1,2,3,3,3-hexafluoropropyl $R^3$ represents hydrogen, cyano, fluorine, chlorine, methyl or ethyl, $R^4$ represents hydrogen, amino, methyl or ethyl, $R^5$ represents hydrogen, methyl, ethyl, isopropyl, tert-butyl, 1-ethyl-1-methylpropyl, 1,1-dimethylpropyl, chloromethyl, difluoromethyl, dichlorofluoromethyl, trifluoromethyl, 3-fluoropropyl, 1,1-dimethyl-2-chloroethyl, 1,1-dimethyl-2-fluoroethyl, cyclopropyl or 1,1-dimethylpropargyl.

3. The phenylacetylene derivatives according to claim 1, wherein

X represents hydrogen or fluorine,

Y represents hydrogen, hydroxy, fluorine, chlorine, cyano, nitro, methyl, trifluoromethyl, methoxy, ethoxy, isopropoxy, cyclopropoxy, cyclopentyloxy, cyclohexyloxy, difluoromethoxy, chlorodifluoromethoxy, trifluoromethoxy, methoxymethoxy, methylthio, ethylthio, isopropylthio, propylthio, cyclopropylthio, cyclopentylthio, difluoromethylthio, chlorodifluoromethylthio, trifluoromethylthio, methylsulfinyl, methylsulfinyl, isopropylsulfonyl, cyclopropylsulfonyl, cyclopentylsulfonyl, difluoromethylsulfonyl, chlorodifluoromethylsulfonyl, trifluoromethylsulfonyl, methylsulfonyloxy, allyloxy, 2-methylallyloxy, propargyloxy, aminosulfonyl, methylaminosulfonyl, ethylaminosulfonyl, a group COOR$^c$, aminocarbonyl, amino, methylsulfonylamino, ethylsulfonylamino, bis(methylsulfonyl)amino, bis(ethylsulfonyl)amino, (acetyl)(ethylsulfonyl)amino, (tert-butyl-carbonyl)(methylsulfonyl)amino, (tert-butylcarbonyl)(ethylsulfonyl)amino, 1-(methoxycarbonyl)ethylthio, ethoxycarbonylmethylthio, methoxycarbonylmethylthio, 1-(ethoxycarbonyl)ethoxy, 1-(methoxycarbonyl)ethoxy, ethoxycarbonylmethoxy, methoxycarbonylmethoxy, 2-(ethoxycarbonyl)-2-chloro-ethoxy ethoxycarbonylmethyl or 2-(ethoxycarbonyl)-2-chloroethyl, $R^c$ represents hydrogen, methyl ethyl propyl, isopropyl, methoxycarbonylmethyl, ethoxycarbonylmethyl, 1-(methoxycarbonyl)ethyl or 1-(ethoxy carbonyl)ethyl, $A^1$ represents oxygen or sulfur, n is 0 or 1, Z represents hydrogen, fluorine or chlorine, m is 1, R represents hydrogen, hydroxymethyl, fluorine, trimethylsilyl, methoxycarbonyl or ethoxycarbonyl, Q represents a heterocycle selected from the group consisting of

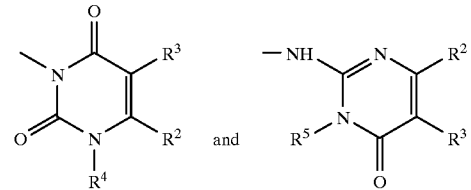

$R^2$ represents hydrogen trifluoromethyl, difluoromethyl, chlorodifluoromethyl or 3-fluoropropyl, $R^3$ represents hydrogen, cyano, fluorine, chlorine or methyl, $R^4$ represents hydrogen, amino or methyl, $R^5$ represents hydrogen, methyl, ethyl, isopropyl, tert-butyl, chloromethyl difluoromethyl, trifluoromethyl, 3-fluoropropyl or cyclopropyl.

4. A herbicidal composition comprising a herbicidally effective amount of a compound according to claim 1 and a diluent.

5. A method of combatting unwanted vegetation which comprises administering to such vegetation or to a locus from which it is desired to exclude such vegetation a herbicidally effective amount of a compound according to claim 1.

* * * * *